(12) United States Patent
Aurisicchio et al.

(10) Patent No.: US 9,688,738 B2
(45) Date of Patent: Jun. 27, 2017

(54) IMMUNOTHERAPY AGAINST ERBB-3 RECEPTOR

(75) Inventors: Luigi Aurisicchio, Rome (IT); Gennaro Ciliberto, Rome (IT); Rita Mancini, Rome (IT); Emanuele Marra, Pomezia (IT); Guiseppe Roscilli, Rome (IT)

(73) Assignee: TAKIS S.R.L., Rome (IT)

( * ) Notice: Subject to any disclaimer, the term of this patent is extended or adjusted under 35 U.S.C. 154(b) by 765 days.

(21) Appl. No.: 13/882,899

(22) PCT Filed: Nov. 2, 2011

(86) PCT No.: PCT/EP2011/005529
§ 371 (c)(1),
(2), (4) Date: Oct. 1, 2013

(87) PCT Pub. No.: WO2012/059224
PCT Pub. Date: May 10, 2012

(65) Prior Publication Data
US 2014/0017259 A1    Jan. 16, 2014

(30) Foreign Application Priority Data
Nov. 2, 2010  (IT) .............................. RM2010A0577

(51) Int. Cl.
| | | |
|---|---|---|
| A61K 39/395 | (2006.01) | |
| C07K 16/30 | (2006.01) | |
| C07K 14/705 | (2006.01) | |
| A61K 38/17 | (2006.01) | |
| A61K 39/00 | (2006.01) | |
| C07K 14/71 | (2006.01) | |
| C07K 16/32 | (2006.01) | |
| A61K 45/06 | (2006.01) | |
| A61K 31/7088 | (2006.01) | |

(52) U.S. Cl.
CPC ........ *C07K 14/705* (2013.01); *A61K 31/7088* (2013.01); *A61K 38/179* (2013.01); *A61K 39/0011* (2013.01); *A61K 45/06* (2013.01); *C07K 14/71* (2013.01); *C07K 16/32* (2013.01); *A61K 2039/507* (2013.01); *A61K 2039/53* (2013.01); *C07K 2317/24* (2013.01); *C07K 2317/34* (2013.01); *C07K 2317/565* (2013.01); *C07K 2317/73* (2013.01); *C07K 2317/76* (2013.01)

(58) Field of Classification Search
CPC .... C07K 16/28; C07K 16/2863; C07K 16/30; C07K 16/46; C07K 16/464; A61K 39/395; A61K 39/39533; A61K 39/3955; A61K 39/39558
See application file for complete search history.

(56) References Cited

U.S. PATENT DOCUMENTS 8,481,687 B2 * 7/2013 Vincent ................. C07K 16/32
530/350
2010/0266584 A1   10/2010 Schoeberl et al.

FOREIGN PATENT DOCUMENTS

| WO |     03/080835     | 10/2003 |            |
|----|-------------------|---------|------------|
| WO |   2006/087637     |  8/2006 |            |
| WO |   2007/077028     |  7/2007 |            |
| WO |   2008/100624     |  8/2008 |            |
| WO |   2009/023266     |  2/2009 |            |
| WO | WO 2011044311 A2 * |  4/2011 | ............. C07K 16/32 |
| WO |   2011/076683     |  6/2011 |            |

OTHER PUBLICATIONS

Almagro & Fransson, Frontiers in Bioscience 2008; 13:1619-33.*
De Genst et al., Dev Comp Immunol 2006; 30:187-98.*
Finlay, W.J., et al., J. Mol. Biol. 388: 541-558, 2009.*
Kani, et al. 2005, Oligomers of ERBB3 have two distinct interfaces that differ in their sensitivity to disruption by heregulin, Journal of Biological Chemistry, 280(9): 8238-8247.
Cambell, et al., (2010) "HER3 Comes of ages: New insights into its functions and role in signaling, tumor biology and cancer therapy," Clinical Cancer Research, 16(5):1373-1383.
Landgraf, et al. (2000) "Heregulin reverses the oligomerization of HER3 +," Biochemistry, 39(29): 8503-8511.
Aurisicchio, et al. (2011) "Novel anti-ErbB3 monoclonal antibodies show therapeutic efficacy in xenographted and spontaneous mouse tumors," Journal of Cellular Physiology, printed online.
Schoeberl, et al. (2010) "An ERB3 antibody, MM-121, is active in cancers with ligand-dependent activiation," Cancer Research, 70(6):2485-2494.
Ciliberto, et al. (2010) "224 Her3 as an emerging target for lung tumor initiating cells," European Journal of Cancer, Supp, 8(7):73.
Cho Hyun-Soo, et al.(2002) "Structure of the extracellular region of HER3 reveals an interdomain tether," Science, 297 (5585): 1330-1333.
Kani, et al. (2005), "the extracellular domains of ErbB3 retain high ligand binding affinity at endosome pH in the locked conformation," Biochemistry, 44(48): 15842-15857.
International Search Report for PCT/EP2011/00529, mailed Feb. 2, 2012.

* cited by examiner

*Primary Examiner* — Misook Yu
*Assistant Examiner* — Anne Holleran
(74) *Attorney, Agent, or Firm* — McDonnell Boehnen Hulbert & Berghoff LLP

(57) ABSTRACT

The present invention describes methods and pharmaceutical compositions for the treatment of cancer in mammals, more particularly in human subjects. More specifically, the invention concerns anti-tumor vaccines based upon plasmid DNA and/or genetic vectors carrying a codon-usage optimized sequence and coding for a mutant form of the ErbB-3 receptor. Furthermore, the invention refers to monoclonal antibodies directed against the ErbB-3 receptor, obtained using these methods and capable to block its activity in cancer cells.

2 Claims, 10 Drawing Sheets

A

B

A

B

A

B

A

B

A

B

A

B

A

B

Fig. 10

Figure 1:
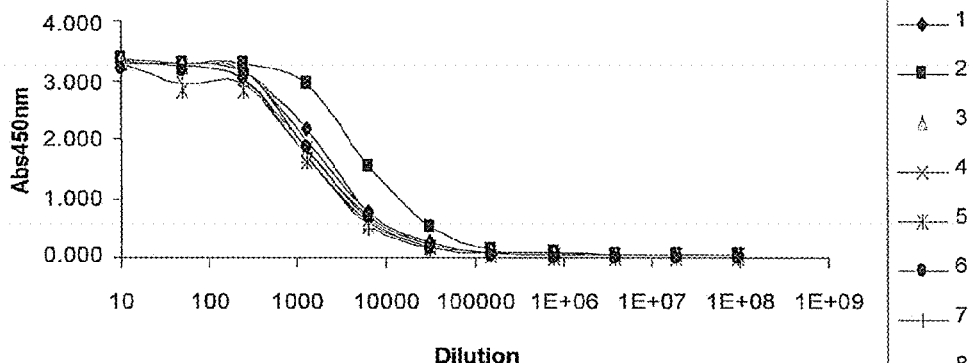

| Antibody | Chain Region | SEQ ID No | Amino Acid Sequence |
|---|---|---|---|
| A3 Mus musculus | Variable light chain region | SEQ 7 | DVLMTQTPLSLPVSLGDQASISCRSSQSIVHSYGNTYLEWYLQKPGQSPKLLIYRVSNRFSGVPDRFSGSGSGTDFTLKISRVEAEDLGVYYCFQGSHVPFTFGTGTKLEIKRADAAPTV<br><br>CDR1 (SEQ 17): RSSQSIVHSYGNTYLE<br>CDR2 (SEQ 18): RVSNRFS<br>CDR3 (SEQ 19): FQGSHVPFT |
| A3 Mus Musculus | Variable heavy chain region | SEQ 8 | QVTLKESGPGKLQPSQTLSLTCSFSGFSLSTYGMGVGWIRQPLGKGLEWLANIWWNDDKYYNSALKSRLTISKDTSNNQVFLKISSVDTADAATYYCVQIANPYWYFDVWGAGTTVTVSSAKTTP<br><br>CDR1 (SEQ 20): TYGMGVG<br>CDR2 (SEQ 21): NIWWNDDKYYNSALKS<br>CDR3 (SEQ 22): IANPYWYFDV |
| A4 Mus musculus | Variable light chain region | SEQ 11 | QIVLTQSPAIMSASPGEKVTMTCRARSSVSSSYLHWYQQKPGSSPKLWIYSTSNLALGVPARFSGSGSGTSYSLTISSVEAEDAATYYCQQYDSSPFTFGTGTKLEIKRADAAPTV<br><br>CDR1 (SEQ 23): RARSSVSSSYLH<br>CDR2 (SEQ 24): STSNLAL<br>CDR3 (SEQ 25): QQYDSSPFT |
| A4 Mus musculus | Variable heavy chain region | SEQ 12 | QVQLQQPGSELVRPGASVKLSCKASGYTFTIFWIHWVKQRPGQGLEWIGNIYPGSGGTNYDEKFKSKATLTVDTFSSTAYMQLSSLTSEDSAVYYCTRWGTGKDYWGQGTTLKVSSAKTTP<br><br>CDR1 (SEQ 26) : IFWIH<br>CDR2 (SEQ 27) : NIYPGSGGTNYDEKFKS<br>CDR3 (SEQ 28) : WGTGKDY |
| A4 humanized | Variable light chain region | SEQ 13 | EIVLTQSPGTLSLSPGERATLSCRASSSVSSSYLHWYQQKPGQAPRLLIYSTSNRATGIPDRFSGSGSGTDFTLTISRLEPEDFAVYYCQQYDSSPFTFGQGTKLEIKR<br><br>CDR1 (SEQ 29) : RASSSVSSSYLH<br>CDR2 (SEQ 30) : STSNRAT<br>CDR3 (SEQ 25) : QQYDSSPFT |
| A4 humanized | Variable heavy chain region | SEQ 14 | QVQLVQSGAEVKKPGASVKVSCKASGYTFTIFWMHWVRQAPGQGLEWMGNIYPGSGGTNYAQKFQGRVTMTRDTSISTAYMELSRLRSDDTVVYYCTRWGTGKDYWGQGTLVTVSS<br>CDR1 (SEQ 31) : IFWMH<br>CDR2 (SEQ 32) : NIYPGSGGTNYAQKFQG<br>CDR3 (SEQ 28) : WGTGKDY |

IMMUNOTHERAPY AGAINST ERBB-3 RECEPTOR

The present invention describes methods and pharmaceutical compositions for the treatment of cancer in mammals, more particularly in human subjects. More specifically, the invention concerns anti-tumor vaccines based upon plasmid DNA and/or genetic vectors carrying a codon-usage optimized sequence and coding for a mutant form of the ErbB-3 receptor. Furthermore, the invention refers to monoclonal antibodies directed against the ErbB-3 receptor, obtained using these methods and capable to block its activity in cancer cells.

BACKGROUND OF THE INVENTION

Research activities in oncology are increasingly directed to identify novel treatments with enhanced specificity against tumors and directed against precise molecular targets (targeted therapy). Indeed very frequently in tumors it is observed that uncontrolled cell growth is due to altered processes of signal transduction from the cell surface that induce cell proliferation, inhibit apoptosis and which frequently involve overexpression and activation of specific surface receptors. The EGFR family (otherwise called ErbB or HER) is constituted by four transmembrane proteins (EGFR/HER1, HER2, HER3 and HER4) which play multiple roles both in normal cells and in the development and maintenance of tumors [1]. Three aberrant mechanisms contribute to the tumorigenic activity of ErbB receptors: receptor overexpression, often linked to gene amplification; constitutive activation due to specific mutation, ligand overexpression. Given the key role of these receptors in oncogenic signalling, new drugs have been developed, both monoclonal antibodies and small molecules, having as targets in particular EGFR and HER2, and which are widely employed in clinical protocols for the therapy of a variety of tumors, mainly lung, colon and breast. Among these, antibodies like cetuximab, panitumumab (against EGFR), trastuzumab and pertuzumab (against HER2) and tyrosine-kinase inhibitors (TKIs) gefitinib, erlotinib (against EGFR) and lapatinib (against EGFR/HER2) [1]. However, in spite of these progresses, the clinical efficacy of these agents is lower than expected and often is accompanied by the emergence of resistance. For example objective responses observed with trastuzumab (HERCEPTIN™) in patients with HER2 positive mammary tumors are low (in general 15%) and short lived [2]. Furthermore, several prototype tumor vaccines against HER2 based mainly upon the use of peptides and proteins have been developed over the last years and tested in Phase I and II clinical trials, without significant results [3,4]. These vaccines had been designed to induce mainly a cell-mediated immune response, with a principal involvement of cytotoxic CD8+ cells (CTLs). The generation of CTL correlated with the prevention and eradication of HER2+ tumor cells in preclinical models, but was unable to control the diffusion of metastasis in human patients. Subsequently, some studies have demonstrated that tumor cells treated simultaneously with trastuzumab and with CTLs derived from patients vaccinated with peptides were lysed more efficiently [5], thus suggesting that an antitumor vaccine against HER2 capable of inducing simultaneously both an antibody response and a cytotoxic response should be able to achieve a significant enhancement of therapeutic efficacy. More recently, genetic vaccines against HER2 based upon plasmid DNA electroporation into muscle tissue and the use of recombinant Adenoviral vectors have been shown to be able to achieve these goals and have provided promising results [6-8], being able to induce at the same time the development of innate immunity, cell-mediated immunity and, most importantly, high titer antibody responses against the receptor.

A distinctive feature of the members of the ErbB receptor family is the interdependence and complementarity of their functions. While HER2 is a known oncogene and its overexpression, mainly linked to gene amplification in approximately 25% of breast tumors, has been causally correlated to tumor development [9], for HER3 no mutations have been found to be directly involved in the process of carcinogenesis. However, loss of HER3 expression abolishes the transforming ability of HER2. Hence, HER3 can be considered as an obligate partner of HER2-mediated transformation [1,10]. Furthermore HER3 seems to play a key role in the development of resistance to current EGFR and HER2 inhibitors, most likely as a consequence of its overexpression and increased plasma membrane localization: its role appears to be linked to the formation of heterodimers with EGFR and with HER2 and its ability to be transphosphorylated in six tyrosine residues that serve as binding sites for molecules involved in the downstream signalling, such as p85, the regulatory subunit of PI3K [11]. Also cMet amplification has recently been described in cells resistant to TKIs, and under this circumstance, the mechanism of resistance seems to be mediated by HER3 transphosphorylation by overexpressed cMet [12]. The PI3K/Akt pathway is critical for the viability and maintenance of cancer stem cells in breast [13], prostate [14], lung [15], colon [16], brain [17] cancers as well as in leukemias [18]. Given the central role of PI3K in the signalling in cancer stem cells and the inability of HER2 to activate the PI3K axis in the absence of HER3, it can be hypothesized that HER3 plays a fundamental role in cancer stem/progenitor cells. Hence, its inhibition may be a powerful strategy to eradicate these cells and improve efficacy of current therapies.

HER3 consists of an extracellular domain which binds to the ligand (ECD), a dimerization domain within the ECD, a transmembrane domain (TM) and a C-terminal domain (ICD), which is phosphorylated. Neuregulin (NRG) or other ligands bind the ECD and trigger signal transduction promoting receptor dimerization with other RTKs and ICD transphosphorylation. Because HER3 does not possess tyrosine kinase activity, its function can only be inhibited by specific monoclonal antibodies. In literature, there are already evidences that antibodies directed against HER3 can display antitumor activity. Schoeberl and coworkers [19,20] have recently shown in primary tumors and in cell lines that express members of the ErbB family and relevant ligands, hence with autocrine loops, that only anti-HER3 antibodies but not antibodies against EGFR (cetuximab), or HER2 (trastuzumab and pertuzumab), are capable to fully inhibit receptor activation induced by all ligands of this receptor family, whereas cetuximab and trastuzumab are able to neutralize only a subset of them.

SUMMARY OF THE INVENTION

In a first aspect the present invention is directed at nucleic acids encoding a variant of HER3, vectors comprising such nucleic acids and methods and tools to block the oncogenic activity of HER3 and of receptors of the ErbB family by using such nucleic acids and vectors. Thus, in a first embodiment, the invention is directed at a new method to induce an immune response against HER3. In particular, the method uses a genetic vaccination which utilizes a vector, for example plasmid DNA, carrying the optimized cDNA for human HER3, expressing the protein with a H584F single amino acid mutation. Such a vector is preferably injected intramuscularly, and following that administration it is preferred that an electric field is applied in order to increase the expression level of the antigen, and to induce in the host organism an antibody and/or cell-mediated immune response against HER3. Such a vaccine, here identified, can be utilized as monotherapy or in combination with chemotherapy (e.g. cisplatin, irinotecan, oxaliplatin), monoclonal antibodies (e.g. Trastuzumab, Pertuzumab, Cetuximab, anti-HER3 antibodies), TKI agents (e.g. gefitinib, erlotinib, lapatinib), immunomodulators (e.g. TLR agonists, MF-59, ipilimumab or other monoclonal antibodies directed against CTLA4) and other antitumor vaccines (e.g. Provenge™, GVAX™).

In a further aspect, the invention is directed to antagonistic monoclonal antibodies generated by the vaccine above which bind the extracellular domain of HER3 and the receptor-dependent signal transduction events, such as pHER3, pAKT and cell proliferation. The nucleotide and amino acid sequence and the process for the generation of these antibodies are described. Expression vectors and host cells which contain them for the production of the antibodies of the invention are also described in detail. Also these biological agents can find application as monotherapy or in combination with other anticancer therapeutics, preferably chemotherapy, other antibodies, TKI agents, immunomodulators and antitumor vaccines. A significant advantage of the invention is based upon the antibody specificity, with known potency. The affinity of the antibodies obtained with this new technology is surprisingly higher than other known antibodies. It is expected that these antibodies can be efficacious in the treatment of patients who have developed resistance to tyrosine-kinase inhibitors, such as TKIs, anti-EGFR antibodies, anti-HER2 antibodies and agents against cMet.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

To practice the present invention, unless otherwise indicated, conventional methods of chemistry, biochemistry, cell biology, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

The term "about" when used in connection with a numerical value is meant to encompass numerical values within a range having a lower limit that is 5% smaller than the indicated numerical value and having an upper limit that is 5% larger than the indicated numerical value.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

An "amino acid substitution" comprises the replacement of one or more amino acids in a protein with another. Substitutions may preserve, diminish or eliminate the protein function. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson [33]. Examples of groups of amino acids that have side chains with similar chemical properties include 1) aliphatic side chains: glycine, alanine, valine, leucine and isoleucine;
2) aliphatic-hydroxyl side chains: serine and threonine;
3) amide-containing side chains: asparagine and glutamine;
4) aromatic side chains: phenylalanine, tyrosine, and tryptophan;
5) basic side chains: lysine, arginine, and histidine;
6) acidic side chains: aspartate and glutamate, and
7) sulfur-containing side chains: cysteine and methionine.

Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. [34]. A "moderately conservative" replacement is any change having a nonnegative value in the PAM250 log-likelihood matrix. Given the known genetic code, and recombinant and synthetic DNA techniques, the skilled scientist can readily construct DNAs encoding conservative amino acid variants. A "non-conservative substitutions" or "non-conservative amino acid exchanges" are defined as exchanges of an amino acid by another amino acid listed in a different group of the seven standard amino acid groups 1) to 7) shown above.

The term "codon", as used herein, refers to a sequence of three nucleotides that encode a specific amino acid within the genetic code.

As used herein, the term "expression vector", refers to an expression construct, which comprises elements for promoting transcription of a desired coding sequence. Preferred examples of expression vectors are selected from the group consisting of a bacterial plasmid, an adenovirus, a poxvirus, a vaccinia virus, a fowlpox virus, a herpes virus, an adeno-associated virus (AAV), an alphavirus, a lentivirus, a lambda phage, a lymphocytic choriomeningitis virus and a *Listeria* sp, *Salmonella* sp., used to introduce a specific gene into a target cell. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments. Once the expression vector is inside the cell, the protein is encoded by the gene. In this application a plasmid vector has been utilized which carries a modified cDNA.

The term "promoter", refers to a DNA region that facilitates the transcription of a particular gene. Promoters are located upstream of the regulated gene (towards the 5' region of the sense strand) and represent critical elements that can work in concert with other regulatory transcriptional elements (e.g. enhancers, silencers, boundary elements, insulators) to direct the level of transcription of a given gene. The term "regulatory transcriptional element" refers to e.g. core promoters, proximal promoters, distal enhancers, silencers, insulators/boundary elements (see, e.g., Maston et al. [35]).

The term "neoplasm" refers to an abnormal mass of tissue as a result of neoplasia which is the abnormal proliferation of cells. If the growth of neoplastic cells exceeds and is not coordinated with that of the normal tissues around it, neoplasm can causes a tumor and/cancer.

The term "genetic vaccine" or "genetic vaccination", as used herein, refers to non-living vaccines that trigger a full immune response. It comprises the direct injection of genetic material into a living host resulting in a small amount of its cells to express the introduced gene products and further resulting in a specific immune activation of the host against the gene delivered antigen (see, e.g., Koprowski et al. [36]).

The term "electroporation" refers to a significant increase in the electrical conductivity and permeability of the cell plasma membrane caused by an externally applied electrical field. In this application the method is used in a preferred embodiment to introduce DNA into a cell according to [21]. Electroporation can be applied in vitro or in vivo.

The term "antibody" typically refers to a glycoprotein comprising at least two heavy (H) chains and two light (L) chains inter-connected by disulfide bonds, or an antigen-binding portion thereof. The term "antibody" also includes all recombinant forms of antibodies. Each heavy chain is comprised of a heavy chain variable region (abbreviated herein as VH or $V_H$) and a heavy chain constant region. Each light chain is comprised of a light chain variable region (abbreviated herein as VL or $V_L$) and a light chain constant region. The VH and VL regions can be further subdivided into regions of hypervariability, termed complementarity determining regions (CDR). Each VH and VL is composed of three CDRs, arranged from amino-terminus to carboxy-terminus in the following order: CDR1, CDR2 and CDR3.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody, e.g. via isolated complementarity determining regions (CDRs), and combinations of two or more isolated CDRs which may optionally be joined by a synthetic linker. Other examples include small antibody mimetics comprising two or more CDR regions that are fused to each other, preferably by cognate framework regions. Such a small antibody mimetic comprising $V_H$ CDR1 and $V_L$ CDR3 linked by the cognate $V_H$ FR2 has been described by Qiu et al. [37].

Antibodies and antigen-binding fragments thereof usable in the invention may be from any animal origin including mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies of the invention may also include chimeric molecules in which an antibody constant region derived from one species, preferably human, is combined with the antigen binding site derived from another species, e.g. mouse. Moreover antibodies of the invention include humanized molecules in which the antigen binding sites of an antibody derived from a non-human species (e.g. from mouse) are combined with constant and framework regions of human origin.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro et al. [38], the content of which is herein incorporated by reference in its entirety. The review article by Almagro et al. [38] is briefly summarized in the following. Almagro et al. [38] distinguish between rational approaches and empirical approaches. Rational approaches are characterized by generating few variants of the engineered antibody and assessing their binding or any other property of interest. If the designed variants do not produce the expected results, a new cycle of design and binding assessment is initiated. Rational approaches include CDR grafting, Resurfacing, Superhumanization, and Human String Content Optimization. In contrast, empirical approaches are based on the generation of large libraries of humanized variants and selection of the best clones using enrichment technologies or high-throughput screening. Accordingly, empirical approaches are dependent on a reliable selection and/or screening system that is able to search through a vast space of antibody variants. In vitro display technologies, such as phage display and ribosome display fulfill these requirements and are well-known to the skilled person. Empirical approaches include FR libraries, Guided selection, Framework-shuffling, and Humaneering.

CDR Grafting

A CDR grafting protocol typically comprises three decision-making points: (1) definition of regions determining the specificity of the donor antibody, i.e. the target for grafting, (2) identification of a source of human sequences to be utilized as FR donors, and (3) selection of residues outside of the region defining the specificity, i.e. determining amino acid positions that are targets for back mutation to restore or improve the affinity of the humanized antibody.

(1) Regions Determining the Antibody Specificity

The experimental structure of the non-human antibody in complex with the antigen provides a detailed map of residues in contact with the antigen and therefore those responsible for determining its specificity. The structural information can be complemented with alanine scanning mutagenesis and/or combinatorial mutagenesis to identify the residues contributing most to the binding energy or to the functional paratope. Since the functional paratope is a subset of the residues in contact, grafting only the functional paratope would reduce the number of non-human residues in the humanized product. However, only in rare cases are the experimental structure of the antigen-antibody complex and/or the functional paratope available at the beginning of a humanization protocol. In absence of a precise definition of residues responsible for a given antibody specificity, CDRs are often employed as regions defining the specificity. It is also possible to use a combination of CDR and HV loop as targets for grafting. To reduce the number of residues to be grafted on the human FRs, SDR grafting has been described, i.e. the grafting of specificity-determining residues (SDRs).

(2) Source of Human FRs

Frame work (FR) regions are more conserved regions within light chains and heavy chain of an antibody. The second step in a typical CDR grafting protocol is to identify human FR donors. Initial works utilized FRs of human antibodies of known structure, regardless of their homology to the non-human antibody. This approach is known as "Fixed FR method". Later works used human sequences having the highest homology to the non-human antibody. This approach has been termed "Best Fit". While "best fit" strategies tend to result in antibodies with higher affinity, other parameters such as low immunogenicity and production yields have to be taken into account, too, when choosing an FR for humanization. Thus, combinations of "best fit" and "fixed FR" are also possible. For example, the $V_L$ part can be humanized according to the fixed FR method and the $V_H$ part can be humanized according to the best fit method, or vice versa.

Two sources of human sequences have been utilized: mature and germline sequences. Mature sequences, which are products of immune responses, carry somatic mutations generated by random processes and are not under the species selection, resulting in potential immunogenic residues. Thus, to avoid immunogenic residues, human germline genes have increasingly been utilized as source of FR donors. Nucleotide sequences of human germline FRs are disclosed e.g. in Appendices A and B of the article by Dall'Acqua et al. [39]. Furthermore, germline gene based antibodies tend to be more flexible as compared to mature antibodies. This higher flexibility is thought to better accommodate diverse CDRs with fewer or no back mutations into the FR to restore the affintiy of the humanized antibody.

(3) Back Mutations to Restore or Enhance Affinity

Commonly, affinity decreases after CDR grafting as a consequence of incompatibilities between non-human CDRs and human FRs. Therefore, the third step in a typical CDR grafting protocol is to define mutations that would restore or prevent affintiy losses. Back mutations have to be carefully designed based on the structure or a model of the humanized antibody and tested experimentally. A web site for automated antibody modeling called WAM can be found at the URL http://antibody.bath.ac.uk. Software for protein structure modeling can be downloaded at the sites http://salilab.org/modeller/modeller.html (Modeller) and http://spdbv.vital-itch (Swiss PdbViewer).

Resurfacing

Resurfacing is similar to CDR grafting and shares the first two decision-making points. In contrast to CDR grafting, resurfacing retains the non-exposed residues of the non-human antibody. Only surface residues in the non-human antibody are changed to human residues.

Superhumanization

While CDR grafting relies on the FR comparison between the non-human and the humans sequences, superhumanization is based on a CDR comparison so that FR homology is irrelevant. The approach includes a comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs [31]. This method is preferred within this application.

Human String Content Optimization

This approach is based on a metric of antibody "humanness", termed Human String Content (HSC). In short, this approach compares the mouse sequence with the repertoire of human germline genes. Differences are scored as HSC. The target sequence is the humanized by maximizing its HSC rather than using a global identity measure to generate multiple diverse humanized variants.

Framework Libraries (Abbreviated: FR Libraries)

In the FR library approach, a collection of residue variants are introduced at specific positions in the FR followed by panning of the library to select the FR that best supports the grafted CDR. Thus, this approach resembles CDR grafting but instead of creating a few back mutations in the FR, a combinatorial library of typically more than 100 mutational variants is constructed.

Guided Selection

This approach includes combining the $V_H$ or $V_L$ domain of a given non-human antibody specific for a particular antigen with a human $V_H$ and $V_L$ library. Subsequently, specific human V domains are selected against the antigen of interest. For example, a non-human antibody can be humanized by first combining the non-human $V_H$ with a library of human light chains. The library is then selected against the target antigen by phage display and the selected $V_L$ is cloned into a library of human $V_H$ chains and selected against the target antigen. It is also possible to start with combining the non-human $V_L$ with a library of human heavy chains. The library is then selected against the target antigen by phage display and the selected $V_H$ is cloned into a library of human $V_L$ chains and selected against the target antigen. As a result, a fully human antibody with similar affinity as the non-human antibody can be isolated. To avoid the occurrence of an epitope drift, it is possible to implement a so-called inhibition ELISA, which allows for the selection of clones recognizing the same epitope as the parent antibody. Alternatively, CDR retention can be applied to avoid an epitope drift. In CDR retention, one or more non-human CDRs are retained, preferably the heavy chain CDR3, since this CDR is at the center of the antigen binding site.

Framework Shuffling (Abbreviated: FR Shuffling)

In the FR shuffling approach, whole FRs are combined with the non-human CDRs. Using FR shuffling, Dall'Acqua and co-workers humanized a murine antibody. All six CDRs of the murine antibody were cloned into a library containing all human germline gene FRs (Dall'Acqua et al. [39]). The libraries were screened for binding in a two-step selection process, first humanizing $V_L$, followed by $V_H$. In a later study, a one-step FR shuffling process was successfully used (Damschroder et al. [40]). Oligonucleotide sequences encoding all known human germline light chain (κ) frameworks are disclosed in Dall'Acqua et al. [39], as Appendix A. Oligonucleotide sequences encoding all known human germline heavy chain frameworks are disclosed in Dall'Acqua et al. [39].

Humaneering

Humaneering allows for isolation of antibodies that are 91-96% homologous to human germline gene antibodies. The method is based on experimental identification of essential minimum specificity determinants (MSDs) and on sequential replacement of non-human fragments into libraries of human FRs and assessment of binding. It begins with regions of the CDR3 of non-human $V_H$ and $V_L$ chains and progressively replaces other regions of the non-human antibody into the human FRs, including the CDR1 and CDR2 of both $V_H$ and $V_L$.

The methods for humanizing antibodies explained above are preferred when generating humanized antibodies that specifically bind to conformational epitopes. Nevertheless, the present invention is not limited to the above-mentioned methods for humanizing antibodies.

Some of the aforementioned humanization methods can be performed without information about the FR sequences in the donor antibody, namely the "Fixed FR Method" (a variant of CDR-grafting), Superhumanization, Framework-shuffling, and Humaneering. Variations of the "fixed FR method" were successfully carried out by Qin et al. [41] and Chang et al. [42]. In particular, Qin et al. [41] constructed an antibody fragment comprising a human heavy chain variable region in which the three CDR regions were replaced by antigenic peptides, which were derived from the CDR sequences of a murine antibody. Chang et al. [42] continued these experiments and constructed an scFv fragment, in which all CDRs from the $V_H$ part and CDR3 from the $V_L$ part were replaced by antigenic peptides, which were derived from the CDR sequences of a murine antibody.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "identity" or "identical," when referring to a nucleic acid or fragment thereof, indicates that, when optimally aligned with appropriate nucleotide insertions or deletions with another nucleic acid (or its complementary strand), there is nucleotide sequence identity in at least about 80%, and more preferably at least about 85%, 90%, 95%, 96%, 97%, 98% or 99% of the nucleotide bases, as measured by any well-known algorithm of sequence identity, such as FASTA, BLAST or GAP, as discussed below.

As applied to polypeptides, the term "identity of XX %" or "identical" means that two peptide sequences, when optimally aligned, such as by the programs GAP or BEST-FIT using default gap weights, share the indicated percentage of identical amino acids. Preferably, the amino aicds share at least 80%, more preferably at least 85%, at least 90% sequence identity, even more preferably at least 95%, 98% or 99% sequence identity. Preferably, residue positions which are not identical differ by conservative amino acid substitutions.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutant thereof, see e.g. GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (see Pearson [43]). Another preferred algorithm when comparing a sequence of the invention to a database containing a large number of sequences from different organisms is the computer program BLAST, especially BLASTP or TBLASTN, using default parameters, see e.g. Altschul et al. [44] which is herein incorporated by reference.

When percentages of sequence identity are referred to in the present application, these percentages are calculated in relation to the full length of the longer sequence, if not specifically indicated otherwise. This calculation in relation to the full length of the longer sequence applies both to nucleic acid sequences and to polypeptide sequences.

The identity in the sequences may be assessed by aligning the polypeptide sequences. Such alignment tools are well known to the person skilled in the art and can be, for example, obtained on the World Wide Web, e.g., ClustalW (www.ebi.ac.uk/clustalw) or Align (http://www.ebi.ac.

uk/_emboss/align/_index.html) using standard settings, preferably for Align EMBOSS::needle, Matrix: Blosum62, Gap Open 10.0, Gap Extend 0.5. The "best sequence alignment" between two polypeptides is defined as the alignment that produces the largest number of aligned identical residues.

In the context of the present invention it is stated that one or more residues in a polypeptide "occupy an analogous position" with respect to one or more residues in a reference polypeptide. It is well known in the art, that analogous positions between a reference polypeptide and one or more further polypeptides can be determined by aligning the polypeptide sequences based on amino acid sequence or structural similarities. Such alignment tools are well known to the person skilled in the art and can be, for example, obtained on the World Wide Web, e.g., ClustalW (www.e-bi.ac.uk/clustalw) or Align (http://www.ebi.ac.uk/emboss/align/index.html) using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment. Once the alignment is completed the relevant residue or residues of the reference polypeptide are identified and the residue or residues of the one or more polypeptides that are aligned with this/these residues can be determined.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in subject.

As used herein, a first compound (e.g. an antibody) is considered to "bind" to a second compound (e.g. an antigen, such as a target protein), if it has a dissociation constant $K_d$ to said second compound of 1 mM or less, preferably 100 µM or less, preferably 50 µM or less, preferably 30 µM or less, preferably 20 µM or less, preferably 10 µM or less, preferably 5 µM or less, more preferably 1 µM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less, even more preferably 8 nM or less, most preferred 8 nM or less.

The term "binding" according to the invention preferably relates to a specific binding. "Specific binding" means that a binding moiety (e.g. an antibody) binds stronger to a target such as an epitope for which it is specific compared to the binding to another target. A binding moiety binds stronger to a first target compared to a second target if it binds to the first target with a dissociation constant ($K_d$) which is lower than the dissociation constant for the second target. Preferably the dissociation constant ($K_d$) for the target to which the binding moiety binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the binding moiety does not bind specifically.

As used herein, the term "$K_d$" (measured in "mol/L", sometimes abbreviated as "M") is intended to refer to the dissociation equilibrium constant of the particular interaction between a binding moiety (e.g. an antibody or fragment thereof) and a target molecule (e.g. an antigen or epitope thereof).

An "epitope", also known as antigenic determinant, is the part of a macromolecule that is recognized by the immune system, specifically by antibodies, B cells, or T cells. As used herein, an "epitope" is the part of a macromolecule capable of binding to a binding moiety (e.g. an antibody or antigen-binding fragment thereof) as described herein. In this context, the term "binding" preferably relates to a specific binding. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

EMBODIMENTS OF THE INVENTION

In the following several aspects of the invention are described in more detail. In this context the meaning of certain terms is further explained and preferred embodiments are indicated. These terms have the same meaning for all aspects of the invention unless the content clearly dictates otherwise. Similarly, the preferred embodiments of one aspect that relates to a similar subject-matter is also a preferred embodiment of another aspect.

In a first aspect the present invention provides a nucleic acid comprising a nucleotide sequence encoding:
(a) a mammalian ErbB3 mutant protein comprising in comparison to the respective wildtype ErbB3 protein an amino acid substitution, which changes the conformation of the extracelluar domain (ECD) of said ErbB3 to an extended conformation;
(b) a N- and/or C-terminal deletion fragment of (a) comprising at least the ECD of the ErbB3 protein; or (c) variant of (a) or (b), which has at least 80%, preferably at least 85%, preferably at least 90%, more preferably at least 91%, more preferably at least 92%, more preferably at least 93%, more preferably at least 94%, more preferably at least 95%, even more preferably at least 96%, even more preferably at least 97%, even more preferably at least 98%, even more preferably at least 99% or most preferably at least 100% amino acid sequence identity to the amino acid of (a) or (b).

Preferably one or more of the nucleotide codons encoding (a), (b) or (c) that occur with low frequency in proteins expressed in mammalian cells have been replaced with nucleotide codons that occur in nucleic acids encoding highly expressed proteins.

The term "ErbB3 mutant protein", as used herein, further refers to a mutant protein comprising an amino acid mutation of ErbB3 protein in comparison to the respective wildtype ErbB3 protein, wherein the nucleic acid sequence of the ErbB3 mutant protein is shown in SEQ ID NO: 2, which changes the conformation of the extracelluar domain (ECD) of said ErbB3 to an extended conformation. As used herein, the term "extracellular domain" (ECD) refers to the domain of the membrane-bound receptor ErbB3 which sticks out of the membrane in to the cytoplasm and therefore on the outside of the cell.

In a preferred embodiment of the first aspect an ErbB3 protein is from a mammal, preferably from rat (Accession No., AAC53050.1), mouse (Accession No., AAA93533.1) or human (Accession No., AAH02706.1), most preferably from human.

It is also preferred that the mutation changes the conformation of the extracellular domain (ECD) of said ErbB3, most preferred to an extended conformation as described in [22]. The conformational change results in a better binding to a ligand, e.g. neuregulin or other ligands which can bind to the ECD of ErbB3 and thus, trigger the signal transduction of ErbB3. The ECD of ErbB3 spans amino acids 20 to 643 according to SEQ ID NO: 2 or amino acids occupying analogous positions in another ErbB3.

It is further preferred that the nucleic acid comprising a nucleotide sequence encoding a deletion fragment of at least the ECD of the ErbB3 protein is the nucleic acid according to SEQ ID NO: 3.

In a preferred embodiment of the nucleic acid of the present invention the following nucleotide codons that occur with low frequency in expressed proteins are replaced with the following nucleotide codons that occur in nucleic acids encoding highly expressed proteins. This feature of the nucleic acid of the invention can alternatively be referred to as codon optimization for expression in mammalian, preferably human cells. Thus, in a preferred embodiment the nucleic acid of the invention is codon optimized for expression in mammalian cells, in particular in humans. In the following a codon usage table for proteins in human cells is indicated.

Codon Usage Table
fields: [triplet] [frequency: per thousand] ([number])
as determined for 93487 coding sequences

| UUU 17.6(714298) | UCU 15.2(618711) | UAU 12.2(495699) | UGU 10.6(430311) |
| UUC 20.3(824692) | UCC 17.7(718892) | UAC 15.3(622407) | UGC 12.6(513028) |
| UUA 7.7(311881) | UCA 12.2(496448) | UAA 1.0(40285) | UGA 1.6(63237) |
| UUG 12.9(525688) | UCG 4.4(179419) | UAG 0.8(32109) | UGG 13.2(535595) |
| CUU 13.2(536515) | CCU 17.5(713233) | CAU 10.9(441711) | CGU 4.5(184609) |
| CUC 19.6(796638) | CCC 19.8(804620) | CAC 15.1(613713) | CGC 10.4(423516) |
| CUA 7.2(290751) | CCA 16.9(688038) | CAA 12.3(501911) | CGA 6.2(250760) |
| CUG 39.6(1611801) | CCG 6.9(281570) | CAG 34.2(1391973) | CGG 11.4(464485) |
| AUU 16.0(650473) | ACU 13.1(533609) | AAU 17.0(689701) | AGU 12.1(493429) |
| AUC 20.8(846466) | ACC 18.9(768147) | AAC 19.1(776603) | AGC 19.5(791383) |
| AUA 7.5(304565) | ACA 15.1(614523) | AAA 24.4(993621) | AGA 12.2(494682) |
| AUG 22.0(896005) | ACG 6.1(246105) | AAG 31.9(1295568) | AGG 12.0(486463) |
| GUU 11.0(448607) | GCU 18.4(750096) | GAU 21.8(885429) | GGU 10.8(437126) |
| GUC 14.5(588138) | GCC 27.7(1127679) | GAC 25.1(1020595) | GGC 22.2(903565) |
| GUA 7.1(287712) | GCA 15.8(643471) | GAA 29.0(1177632) | GGA 16.5(669873) |
| GUG 28.1(1143534) | GCG 7.4(299495) | GAG 39.6(1609975) | GGG 16.5(669768) |

These numbers translate to the following preferred replacements of low or lower frequency codons, with higher or highest frequency codons. The most preferred replacements are highlighted:

| Encoded Amino Acid | Low or lower Frequency Codon to be replaced | Higher or highest Frequency Codon |
|---|---|---|
| Phe | UUU 17.6(714298) | UUC 20.3(824692) |
| Leu | CUA 7.2(290751) | UUA 7.7(311881) |
| Leu | CUA 7.2(290751) | UUG 12.9(525688) |
| Leu | CUA 7.2(290751) | CUU 13.2(536515) |
| Leu | CUA 7.2(290751) | CUC 19.6(796638) |
| Leu | CUA 7.2(290751) | CUG 39.6(1611801) |
| Leu | UUA 7.7(311881) | UUG 12.9(525688) |
| Leu | UUA 7.7(311881) | CUU 13.2(536515) |
| Leu | UUA 7.7(311881) | CUC 19.6(796638) |
| Leu | UUA 7.7(311881) | CUG 39.6(1611801) |
| Leu | UUG 12.9(525688) | CUU 13.2(536515) |
| Leu | UUG 12.9(525688) | CUC 19.6(796638) |
| Leu | UUG 12.9(525688) | CUG 39.6(1611801) |
| Leu | CUU 13.2(536515) | CUC 19.6(796638) |
| Leu | CUU 13.2(536515) | CUG 39.6(1611801) |
| Leu | CUC 19.6(796638) | CUG 39.6(1611801) |
| Ile | AUA 7.5(304565) | AUU 16.0(650473) |
| Ile | AUA 7.5(304565) | AUC 20.8(846466) |
| Ile | AUU 16.0(650473) | AUC 20.8(846466) |
| Val | GUA 7.1(287712) | GUU 11.0(448607) |
| Val | GUA 7.1(287712) | GUC 14.5(588138) |
| Val | GUA 7.1(287712) | GUG 28.1(1143534) |
| Val | GUU 11.0(448607) | GUC 14.5(588138) |
| Val | GUU 11.0(448607) | GUG 28.1(1143534) |
| Val | GUC 14.5(588138) | GUG 28.1(1143534) |
| Ser | UCG 4.4(179419) | AGU 12.1(493429) |
| Ser | UCG 4.4(179419) | UCA 12.2(496448) |
| Ser | UCG 4.4(179419) | UCU 15.2(618711) |
| Ser | UCG 4.4(179419) | UCC 17.7(718892) |
| Ser | UCG 4.4(179419) | AGC 19.5(791383) |
| Ser | AGU 12.1(493429) | UCA 12.2(496448) |
| Ser | AGU 12.1(493429) | UCU 15.2(618711) |
| Ser | AGU 12.1(493429) | UCC 17.7(718892) |
| Ser | AGU 12.1(493429) | AGC 19.5(791383) |
| Ser | UCA 12.2(496448) | UCU 15.2(618711) |
| Ser | UCA 12.2(496448) | UCC 17.7(718892) |
| Ser | UCA 12.2(496448) | AGC 19.5(791383) |
| Ser | UCU 15.2(618711) | UCC 17.7(718892) |
| Ser | UCU 15.2(618711) | AGC 19.5(791383) |
| Ser | UCC 17.7(718892) | AGC 19.5(791383) |
| Pro | CCG 6.9(281570) | CCA 16.9(688038) |
| Pro | CCG 6.9(281570) | CCU 17.5(713233) |
| Pro | CCG 6.9(281570) | CCC 19.8(804620) |
| Pro | CCA 16.9(688038) | CCU 17.5(713233) |
| Pro | CCA 16.9(688038) | CCC 19.8(804620) |
| Pro | CCU 17.5(713233) | CCC 19.8(804620) |
| Thr | ACG 6.1(246105) | ACU 13.1(533609) |

-continued

| Encoded Amino Acid | Low or lower Frequency Codon to be replaced | Higher or highest Frequency Codon |
|---|---|---|
| Thr | ACG 6.1(246105) | ACA 15.1(614523) |
| Thr | ACG 6.1(246105) | ACC 18.9(768147) |
| Thr | ACU 13.1(533609) | ACA 15.1(614523) |
| Thr | ACU 13.1(533609) | ACC 18.9(768147) |
| Thr | ACA 15.1(614523) | ACC 18.9(768147) |
| Ala | GCG 7.4(299495) | GCA 15.8(643471) |
| Ala | GCG 7.4(299495) | GCU 18.4(750096) |
| Ala | GCG 7.4(299495) | GCC 27.7(1127679) |
| Ala | GCA 15.8(643471) | GCU 18.4(750096) |
| Ala | GCA 15.8(643471) | GCC 27.7(1127679) |
| Ala | GCU 18.4(750096) | GCC 27.7(1127679) |
| Tyr | UAU 12.2(495699) | UAC 15.3(622407) |
| Stopp | UAG 0.8(32109) | UAA 1.0(40285) |
| Stopp | UAG 0.8(32109) | UGA 1.6(63237) |
| Stopp | UAA 1.0(40285) | UGA 1.6(63237) |
| His | CAU 10.9(441711) | CAC 15.1(613713) |
| Gln | CAA 12.3(501911) | CAG 34.2(1391973) |
| Asn | AAU 17.0(689701) | AAC 19.1(776603) |
| Lys | AAA 24.4(993621) | AAG 31.9(1295568) |
| Asp | GAU 21.8(885429) | GAC 25.1(1020595) |
| Glu | GAA 29.0(1177632) | GAG 39.6(1609975) |
| Cys | UGU 10.6(430311) | UGC 12.6(513028) |
| Arg | CGU 4.5(184609) | CGA 6.2(250760) |
| Arg | CGU 4.5(184609) | CGC 10.4(423516) |
| Arg | CGU 4.5(184609) | CGG 11.4(464485) |
| Arg | CGU 4.5(184609) | AGG 12.0(486463) |
| Arg | CGU 4.5(184609) | AGA 12.2(494682) |
| Arg | CGA 6.2(250760) | CGC 10.4(423516) |
| Arg | CGA 6.2(250760) | CGG 11.4(464485) |
| Arg | CGA 6.2(250760) | AGG 12.0(486463) |
| Arg | CGA 6.2(250760) | AGA 12.2(494682) |
| Arg | CGC 10.4(423516) | CGG 11.4(464485) |
| Arg | CGC 10.4(423516) | AGG 12.0(486463) |
| Arg | CGC 10.4(423516) | AGA 12.2(494682) |
| Arg | CGG 11.4(464485) | AGG 12.0(486463) |
| Arg | CGG 11.4(464485) | AGA 12.2(494682) |
| Arg | AGG 12.0(486463) | AGA 12.2(494682) |
| Gly | GGU 10.8(437126) | GGG 16.5(669768) |
| Gly | GGU 10.8(437126) | GGA 16.5(669873) |
| Gly | GGU 10.8(437126) | GGC 22.2(903565) |
| Gly | GGG 16.5(669768) | GGA 16.5(669873) |
| Gly | GGG 16.5(669768) | GGC 22.2(903565) |
| Gly | GGA 16.5(669873) | GGC 22.2(903565) |

It is preferred that at least 10% of all low or lower frequency codons are replaced by high or higher frequency codons, more preferably at least 20%, 30%, 40%, 50%, 60%, 70%, 80%, 90% or 100%. In a particular preferred embodiment all low or lower frequency codons are replaced with the respective highest frequency codon encoding a given amino acid. The resulting nucleic acid, thus, differs from the naturally occurring nucleic acid but encodes the identical protein but for the substitution discussed above.

In a preferred embodiment of the first aspect of the present invention, the amino acid at position 584 according to SEQ ID NO: 2 or at an amino acid occupying an analogous position is mutated to another amino acid, preferably to Gly, Ala, Val, Cys, Arg, Pro, Ser, Leu, Ile, Met, Tyr, Thr, Trp, Gln, Asn, Asp, Glu, Lys, or Phe, most preferably to Phe It is also preferred that the encoded polypeptide is selected from the group consisting of SEQ ID NO: 2 and SEQ ID NO: 4.

In a second aspect the present invention is directed to an expression vector comprising the nucleic acid of the first aspect of the invention, operatively linked to a promoter or to a regulatory transcriptional element. For example, to a promoter which is a regulatory region of the DNA which is located upstream (towards the 5' region of the sense strand) of a gene, facilitating the transcription of a gene. The structure of gene promoters can be quite complex, typically consisting of multiple transcriptional regulatory elements, for example core promoters, proximal promoters, distal enhancers, silencers, insulators/boundary elements, for further information see Maston et al. [34].

In a preferred embodiment, the expression vector is selected from the group consisting of a bacterial plasmid, an adenovirus, a poxvirus, a vaccinia virus, a fowlpox virus, a herpes virus, an adeno-associated virus (AAV), an alphavirus, a lentivirus, a lambda phage, a lymphocytic choriomeningitis virus and a *Listeria* sp, *Salmonella* sp.

In a third aspect the present invention is directed to a nucleic acid of the first aspect or an expression vector of the second aspect for use in preventing, treating or delaying neoplasms in a mammal. Thus, the present invention relates to a method of preventing, treating or delaying neoplasm in a mammal, wherein an effective amount of said nucleic acid or expression vector is administered to a subject in need thereof. Neoplasm is uncontrolled cell growth as a result of neoplasia which means abnormal proliferation of cells. Neoplasm can cause a tumor and/or cancer.

In a further embodiment of this aspect the present invention is directed to a nucleic acid or an expression vector, wherein one or more of the nucleotide codons of the nucleotide encoding the protein according to (a), (b) or (c) is a nucleotide codon that occurs with low frequency in proteins expressed in mammalian cells have been replaced with nucleotide codons that occur in nucleic acids encoding highly expressed proteins.

In a further embodiment of this aspect an immune response, preferably a T and/or B cell response is generated against said neoplasm.

In a further embodiment of this aspect the mammal is a human, mouse, rat, dog, cat, horse, more prefeably human, mouse, rat or dog, most preferred human.

In a preferred embodiment of this aspect the nucleic acid comprises a nucleotide sequence set forth in SEQ ID NO: 1 or SEQ ID NO: 3.

It is preferred that the nucleic acid or expression vector is administered parenteral. Parenteral administration preferably comprises intramuscular, subcutan, intradermal, intraarterial, intrasternal, intracranial, intrathoracic, intraspinal and/or into the neoplasm in situ. The most preferred administration is intramuscular.

It is preferred that the administration further comprises the step of applying electroporation, preferably to the site of administration of the nucleic acid or expression vector.

It is also preferred to administering an immune response potentiator to the mammal. This may be administered prior, concomittantly or after administration of the nucleic acid or expression vector of the invention. For administration the nucleic acid or expression vector can be combined with one or more adjuvants for the route of administration, e.g. dissolved in saline.

Preferably. the nucleic acid or the expression vector is co-administered with an anti-neoplastic agent or antineoplatic regimen. Preferably, the anti-neoplastic agent is selected from the group consisting of an anti-angiogenic agent, an alkylating agent, an antimetabolite, a natural product, a platinum coordination complex, an anthracenedione, a substituted urea, a methylhydrazine derivative, an adrenocortical suppressant, a hormone, an antagonist, an oncogene inhibitor, a tumor suppressor gene or protein, a therapeutic antibody and an anti-oncogene oligonucleotide.

Neoplasm to be prevented, treated or delayed is selected from the group consisting of adrenal gland, anus, auditory nerve, bile ducts, bladder, bone, brain, breast, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharinx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve and vulva neoplasm, preferably breast cancer, preferably lung cancer, preferably pancreatic cancer, preferably ovarian cancer, preferably gastric cancer, preferably prostate cancer or melanoma.

In a fourth aspect the present invention is directed to a method of generating an antibody against mammalian ErbB3 comprising the step of administering to a mammal:
(a) a mammalian ErbB3 mutant protein comprising in comparison to the respective wildtype ErbB3 protein an amino acid substitution, which changes the conformation of the extracelluar domain (ECD) of said ErbB3 to an extended conformation,
(b) a N- and/or C-terminal deletion fragment of (a) comprising at least the ECD of the ErbB3 protein; or
(c) a variant of (a) or (b), which has at least 80%, preferably at least 85%, preferably at least 90%, more preferably at least 91%, more preferably at least 92%, more preferably at least 93%, more preferably at least 94%, more preferably at least 95%, even more preferably at least 96%, even more preferably at least 97%, even more preferably at least 98%, even more preferably at least 99% or most preferably at least 100% amino acid sequence identity to the amino acid of (a) or (b) or a nucleotide encoding the protein according to (a), (b) or (c).

It is preferred in this method that one or more of the nucleotide codons of the nucleotide encoding the protein according to (a), (b) or (c) is a nucleotide codon that occurs with low frequency in proteins expressed in mammalian cells have been replaced with nucleotide codons that occur in nucleic acids encoding highly expressed proteins.

In a fifth aspect the present invention relates to an antibody produced or producible according to the method of the present invention, wherein the antibody binds to an epitope in an extracellular domain of the ErbB3 protein, or a functional fragment thereof and exhibits one or more of the following properties: i. inhibition of heregulin, epiregulin, betacellulin, epigen or biregulin-mediated signalling through ErbB3 which can be measured according to the methods of the present invention; ii. inhibition of proliferation of cells expressing ErbB3 which can be measured according to the methods of the present invention or other methods which are well known in the art for the skilled person (e.g. cell proliferation assays which can be obtained by Invitrogen, Promega or other chemical companies familiar to those skilled in the art); iii. the ability to decrease levels of ErbB3 on cell surfaces which can be measured according to the methods of the present invention; iv. inhibition of VEGF secretion of cells expressing ErbB3 which can be measured according to the methods of the present invention or other methods which are well-known for the skilled person (e.g. ELISA assay which can be obtained from Millipore or other chemical companies familiar to those skilled in the art); v. inhibition of the migration of cells expressing ErbB3 which can be measured according to the methods of the present invention or migration assay which are well-known for the skilled person (see e.g. migration assays which can be obtained from Millipore or other chemical companies familiar to those skilled in the art); vi. inhibition of spheroid growth of cells expressing ErbB3 which can be measured according to the methods of the present invention; vii. a binding specificity to ErbB3 of 20 nM or less, preferably 10 nM or less more preferably 8 nM or less which can be measured according to the methods of the present invention other methods which are well known in the art for the skilled person, e.g. by SPR on a biacore (sodium plasmon resonance on a biacore, see e.g., Maier S. A. et al. [45]); or viii. inhibits homo- and/or heterodimerization of ErbB3.

Preferably the antibody of the invention comprises the following properties (i) and (ii); (i), (ii) and (iii); (i), (ii), (iii) and (iv); (i), (ii), (iii), (iv), and (v); (i), (ii), (iii), (iv), (v), and (vi); (i), (ii), (iii), (iv), (v), (vi), and (vii); (i), (ii), (iii), (iv), (v), (vi), (vii), and (viii); (ii), (iii), (iv), (v), (vi), (vii), and (viii); (iii), (iv), (v), (vi), (vii), and (viii); (iv), (v), (vi), (vii), and (viii); (vi), (vii), and (viii); (vii), and (viii); (i), (iii), (iv), (v), (vi), (vii), and (viii); (i), (iv), (v), (vi), (vii), and (viii); (i), (v), (vi), (vii), and (viii); (i), (vii), and (viii); (i), and (viii); (i), (ii), (iv), (v), (vi), (vii), and (viii); (i), (ii), (v), (vi), (vii), and (viii); (i), (ii), (vi), (vii), and (viii); (i), (ii), (vii), and (viii); (i), (ii), and (viii); (i), (ii), (iii), (v), (vi), (vii), and (viii); (i), (ii), (iii), (vi), (vii), and (viii); (i), (ii), (iii), (vii), and (viii); (i), (ii), (iii), and (viii); (i), (ii), (iii), (iv), (vi), (vii), and (viii); (i), (ii), (iii), (iv), (vii), and (viii); (i), (ii), (iii), (iv), (v), (vii), and (viii); (i), (ii), (iii), (iv), (v), (vi), (vii), and (viii); (i), (ii), (iii), (iv), (v), (vi), and (viii); (ii), (iv), (v), (vi), (vii), and (viii); (ii), (v), (vi), (vii), and (viii); (ii), (vi), (vii), and (viii); (ii), (vii), and (viii); (ii), and (viii); (ii), (iii), (v), (vi), (vii), and (viii); (ii), (iii), (vi), (vii), and (viii); (ii), (iii), (vii), and (viii); (ii), (iii), and (viii); (ii), (iii), (iv), (vi), (vii), and (viii); (ii), (iii), (iv), (vii), and (viii); (ii), (iii), (iv), and (viii); or (ii), (iii), (iv), (v), (vii), and (viii); (ii), (iii), (iv), (v), (viii).

In a preferred embodiment the antibody of the present invention specifically binds to:
(i) an epitope of human ErbB3 which is formed by the amino acid sequences spanning positions 215 to 227 of human ErbB3 according to SEQ ID NO: 2,
(ii) to an epitope that occupies analogous positions to amino acids 215 to 227 of SEQ ID NO: 2 in another ErbB3 protein
(iii) or an at least 8 amino acid long fragment of (i) or (ii). In this context the term "specifically binds to" refers to a binding specificity of at least 1000 nM, preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, even more preferably 10 nM or less, even more preferably 8 nM or less, most preferably 8 nM or less.

Preferably the epitope of ErbB3 is an at least 8 amino acid long fragment comprising the following amino acids QCNGHCFG (SEQ ID NO: 33), CNGHCFGP (SEQ ID NO: 34), NGHCFGPN (SEQ ID NO: 35), GHCFGPNP (SEQ ID NO: 36), HCFGPNPN (SEQ ID NO: 37), CFGPNPNQ (SEQ ID NO: 38), FGPNPNQC (SEQ ID NO: 39) or GPNPNQCC (SEQ ID NO: 40), preferably the epitope of ErbB3 is an at least 9 amino acid long fragment comprising the following amino acids QCNGHCFGP (SEQ ID NO: 41), CNGHCFGPN (SEQ ID NO: 42), NGHCFGPNP (SEQ ID NO: 43), GHCFGPNPN (SEQ ID NO: 44), HCFGPNPNQ (SEQ ID NO: 45), CFGPNPNQC (SEQ ID NO: 46) or FGPNPNQCC (SEQ ID NO: 47), preferably the epitope of ErbB3 is an at least 10 amino acid long fragment comprising the following amino acids QCNGHCFGPN (SEQ ID NO: 48), CNGHCFGPNP (SEQ ID NO: 49), NGHCFGPNPN (SEQ ID NO: 50), GHCFGPNPNQ (SEQ ID NO: 51), HCFGPNPNQC (SEQ ID NO: 52) or CFGPNPNQCC (SEQ ID NO: 53), preferably the epitope of ErbB3 is an at least 11 amino acid long fragment comprising the following amino acids QCNGHCFGPNP (SEQ ID NO: 54), CNGHCFGPNPN (SEQ ID NO: 55), NGHCFGPNPNQ (SEQ ID NO: 56), GHCFGPNPNQC (SEQ ID NO: 57) or HCFGPNPNQCC (SEQ ID NO: 58), preferably the epitope of ErbB3 is an at least 12 amino acid long fragment comprising the following amino acids QCNGHCFGPNPN (SEQ ID NO: 59), CNGHCFGPNPNQ (SEQ ID NO: 60), NGHCFGPNPNQC (SEQ ID NO: 61) or GHCFGPNPNQCC (SEQ ID NO: 62), preferably the epitope of ErbB3 is an at least 13 amino acid long fragment comprising the following amino acids QCNGHCFGPNPNQ (SEQ ID NO: 63), CNGHCFGPNPNQC (SEQ ID NO: 64) or NGHCFGPNPNQCC (SEQ ID NO: 65), preferably the epitope of ErbB3 is an at least 14 amino acid long fragment comprising the following amino acids CNGHCFGPNPNQCC (SEQ ID NO: 66) or QCNGHCFGPNPNQC (SEQ ID NO: 67), preferably the epitope of ErbB3 is an at least 15 amino acid long fragment comprising the following amino acids QCNGHCFGPNPNQCC (SEQ ID NO: 68), most preferably the epitope of ErbB3 is an at least 15 amino acid long fragment comprising the following amino acids QCNGHCFGPNPNQCC (SEQ ID NO: 68). This epitope spans amino acids 215 to 227 of human ErbB3 according to SEQ ID NO: 2. Alternatively, the ErbB3 epitope to which the antibodies of the invention bind is an epitope that occupies analogous positions to amino acids 215 to 227 of SEQ ID NO: 2 in another ErbB3 protein.

In a preferred embodiment the antibody of present invention comprises: (i) a light chain CDR3 sequence as set forth in SEQ ID NO: 19 or a sequence, which comprises with respect to SEQ ID NO: 19 one or two amino acid substitutions, deletions and/or insertions, preferably one or two amino acid substitutions; or (ii) a light chain CDR3 sequence as set forth in SEQ ID NO: 25 or a sequence, which comprises with respect to SEQ ID NO: 25 one or two amino acid substitutions, deletions and/or insertions, preferably one or two amino acid substitutions. In this context it is preferred that the antibody or antigen-binding fragment thereof further comprises: (i) a light chain CDR1 sequence according to SEQ ID NO: 17 or a sequence, which comprises with respect to SEQ ID NO: 17 one, two or three amino acid substitutions, deletions and/or insertions, preferably one, two or three amino acid substitutions; (ii) a light chain CDR1 sequence according to SEQ ID NO: 23 or a sequence, which comprises with respect to SEQ ID NO: 23 one, two or three amino acid substitutions, deletions and/or insertions, preferably one, two or three amino acid substitutions; (iii) a light chain CDR2 sequence according to SEQ ID NO: 18 or a sequence, which comprises with respect to SEQ ID NO: 18 one or two amino acid substitutions, deletions and/or insertions, preferably one or two amino acid substitutions; (iv) a light chain CDR2 sequence according to SEQ ID NO: 24 or a sequence, which comprises with respect to SEQ ID NO: 24 one or two amino acid substitutions, deletions and/or insertions, preferably one or two amino acid substitutions; (v) a heavy chain CDR1 sequence according to SEQ ID NO: 20 or a sequence, which comprises with respect to SEQ ID NO: 20 one, two or three amino acid substitutions, deletions and/or insertions, preferably one, two or three amino acid substitutions; (vi) a heavy chain CDR1 sequence according to SEQ ID NO: 26 or a sequence, which comprises with respect to SEQ ID NO: 26 one, two or three amino acid substitutions, deletions and/or insertions, preferably one, two or three amino acid substitutions; (vii) a heavy chain CDR2 sequence according to SEQ ID NO: 21 or a sequence, which comprises with respect to SEQ ID NO: 21 one or two amino acid substitutions, deletions and/or insertions, preferably one or two amino acid substitutions; (viii) a heavy chain CDR2 sequence according to SEQ ID NO: 27 or a sequence, which comprises with respect to SEQ ID NO: 27 one or two amino acid substitutions, deletions and/or insertions, preferably one or two amino acid substitutions; a heavy chain CDR3 sequence according to SEQ ID NO: 22 or a sequence, which comprises with respect to SEQ ID NO: 22 one or two amino acid substitutions, deletions and/or insertions; preferably one or two amino acid substitutions; (x) a heavy chain CDR3 sequence according to SEQ ID NO: 28 or a sequence, which comprises with respect to SEQ ID NO: 28 one or two amino acid substitutions, deletions and/or insertions, preferably one or two amino acid substitutions; (xi) a light chain CDR1 sequence according to SEQ ID NO: 29 or a sequence, which comprises with respect to SEQ ID NO: 29 one, two or three amino acid substitutions, deletions and/or insertions, preferably one, two or three amino acid substitutions; (xii) a light chain CDR2 sequence according to SEQ ID NO: 30 or a sequence, which comprises with respect to SEQ ID NO: 30 one or two amino acid substitutions, deletions and/or insertions, preferably one or two amino acid substitutions; (xiii) a heavy chain CDR1 sequence according to SEQ ID NO: 31 or a sequence, which comprises with respect to SEQ ID NO: 31 one, two or three amino acid substitutions, deletions and/or insertions, preferably one, two or three amino acid substitutions; (xiv) a heavy chain CDR2 sequence according to SEQ ID NO: 32 or a sequence, which comprises with respect to SEQ ID NO: 32 one or two amino acid substitutions, deletions and/or insertions, preferably one or two amino acid substitutions.

In a preferred embodiment the antibody or an antigen-binding fragment thereof comprises: (a) a heavy chain CDR3 sequence as set forth in SEQ ID NO: 22 or a sequence, which comprises with respect to SEQ ID NO: 22 one or two amino acid substitutions, deletions and/or insertions, preferably one or two amino acid substitutions; or (b) a heavy chain CDR3 sequence as set forth in SEQ ID NO: 28 or a sequence, which comprises with respect to SEQ ID NO: 28 one or two amino acid substitutions, deletions and/or insertions, preferably one or two amino acid substitutions. In this context it is preferred that the antibody or antigen-binding fragment thereof further comprises: (a) a light chain CDR1 sequence according to SEQ ID NO: 17 or a sequence, comprises with respect to SEQ ID NO: 17 one, two or three amino acid substitutions, deletions and/or insertions, preferably one, two or three amino acid substitutions; (b) a light chain CDR1 sequence according to SEQ ID NO: 23 or a sequence, which comprises with respect to SEQ ID NO: 23 one, two or three amino acid substitutions, deletions and/or insertions, preferably one, two or three amino acid substitutions; (c) a light chain CDR2 sequence according to SEQ ID NO: 18 or a sequence, which comprises with respect to SEQ ID NO: 18 one or two amino acid substitutions, deletions and/or insertions, preferably one or two amino acid substitutions; (d) a light chain CDR2 sequence according to SEQ ID NO: 24 or a sequence, which comprises with respect to SEQ ID NO: 24 one or two amino acid substitutions, deletions and/or insertions, preferably one or two amino acid substitutions; (e) a light chain CDR3 sequence according to SEQ ID NO: 19 or a sequence, which comprises with respect to SEQ ID NO: 19 one or two amino acid substitutions, deletions and/or insertions, preferably one or two amino acid substitutions; (f) a light chain CDR3 sequence according to SEQ ID NO: 25 or a sequence, which comprises with respect to SEQ ID NO: 25 one or two amino acid substitutions, deletions and/or insertions, preferably one or two amino acid substitutions; (g) a heavy chain CDR1 sequence according to SEQ ID NO: 20 or a sequence, which comprises with respect to SEQ ID NO: 20 one, two or three amino acid substitutions, deletions and/or insertions, preferably one, two or three amino acid substitutions; (h) a heavy chain CDRI sequence according to SEQ ID NO: 26 or a sequence, which comprises with respect to SEQ ID NO: 26 one, two or three amino acid substitutions, deletions and/or insertions, preferably one, two or three amino acid substitutions; (i) a heavy chain CDR2 sequence according to SEQ ID NO: 21 or a sequence, which comprises with respect to SEQ ID NO: 21 one or two amino acid substitutions, deletions and/or insertions, preferably one or two amino acid substitutions; (j) a heavy chain CDR2 sequence according to SEQ ID NO: 27 or a sequence, which comprises with respect to SEQ ID NO: 27 one or two amino acid substitutions, deletions and/or insertions, preferably one or two amino acid substitutions; (k) a light chain CDRI sequence according to SEQ ID NO: 29 or a sequence, which comprises with respect to SEQ ID NO: 29 one, two or three amino acid substitutions, deletions and/or insertions, preferably one, two or three amino acid substitutions; (l) a light chain CDR2 sequence according to SEQ ID NO: 30 or a sequence, which comprises with respect to SEQ ID NO: 30 one or two amino acid substitutions, deletions and/or insertions, preferably one or two amino acid substitutions; (m) a heavy chain CDR1 sequence according to SEQ ID NO: 31 or a sequence, which comprises with respect to SEQ ID NO: 31 one, two or three amino acid substitutions, deletions and/or insertions, preferably one, two or three amino acid substitutions; (n) a heavy chain CDR2 sequence according to SEQ ID NO: 32 or a sequence, which comprises with respect to SEQ ID NO: 32 one or two amino acid substitutions, deletions and/or insertions, preferably one or two amino acid substitutions.

In a preferred embodiment of the antibody of the invention or antigen-binding fragment thereof it comprises one of the sets of heavy chain CDR3, heavy chain CDR2, and heavy chain CDR1 sequences as listed below in Table 1, wherein each heavy chain CDR3 sequence comprises one or two amino acid substitutions, deletions and/or insertions, preferably one or two amino acid substitutions as listed in Table 1; wherein each heavy chain CDR2 sequence comprises one or two amino acid substitutions, deletions and/or insertions, preferably one or two amino acid substitutions as listed in Table 1; and wherein each heavy chain CDRI sequence comprises with respect to SEQ ID NO: 30 one, two or three amino acid substitutions, deletions and/or insertions, preferably one, two or three amino acid substitutions as listed in Table 1.

TABLE 1

Sets of heavy chain CDR sequences suitable for use in the antibodies or fragments thereof of the present invention

| Symbol of heavy chain set | CDR3 sequence | CDR2 sequence | CDR1 sequence |
|---|---|---|---|
| A | SEQ ID NO: 22 | SEQ ID NO: 21 | SEQ ID NO: 20 |
| B | SEQ ID NO: 22 | SEQ ID NO: 21 | SEQ ID NO: 26 |
| C | SEQ ID NO: 22 | SEQ ID NO: 27 | SEQ ID NO: 26 |

TABLE 1-continued

Sets of heavy chain CDR sequences suitable for use in the antibodies or fragments thereof of the present invention

| Symbol of heavy chain set | CDR3 sequence | CDR2 sequence | CDR1 sequence |
|---|---|---|---|
| D | SEQ ID NO: 22 | SEQ ID NO: 27 | SEQ ID NO: 20 |
| E | SEQ ID NO: 28 | SEQ ID NO: 21 | SEQ ID NO: 20 |
| F | SEQ ID NO: 28 | SEQ ID NO: 27 | SEQ ID NO: 20 |
| G | SEQ ID NO: 28 | SEQ ID NO: 27 | SEQ ID NO: 26 |
| H | SEQ ID NO: 28 | SEQ ID NO: 21 | SEQ ID NO: 26 |
| I | SEQ ID NO: 22 | SEQ ID NO: 21 | SEQ ID NO: 31 |
| J | SEQ ID NO: 22 | SEQ ID NO: 32 | SEQ ID NO: 31 |
| K | SEQ ID NO: 22 | SEQ ID NO: 32 | SEQ ID NO: 20 |
| L | SEQ ID NO: 28 | SEQ ID NO: 32 | SEQ ID NO: 31 |
| M | SEQ ID NO: 28 | SEQ ID NO: 27 | SEQ ID NO: 31 |
| N | SEQ ID NO: 28 | SEQ ID NO: 32 | SEQ ID NO: 26 |
| O | SEQ ID NO: 22 | SEQ ID NO: 27 | SEQ ID NO: 31 |
| P | SEQ ID NO: 28 | SEQ ID NO: 21 | SEQ ID NO: 31 |
| Q | SEQ ID NO: 22 | SEQ ID NO: 32 | SEQ ID NO: 26 |
| R | SEQ ID NO: 28 | SEQ ID NO: 32 | SEQ ID NO: 20 |

In a preferred embodiment of the antibody of the invention or antigen-binding fragment thereof it comprises one of the sets of light chain CDR3, light chain CDR2, and light chain CDR1 sequences as listed below in Table 2, wherein each light chain CDR3 sequence comprises one or two amino acid substitutions, deletions and/or insertions, preferably one or two amino acid substitutions as listed in Table 2; wherein each light chain CDR2 sequence comprises one or two amino acid substitutions, deletions and/or insertions, preferably one or two amino acid substitutions as listed in Table 2; and wherein each light chain CDR1 sequence comprises one, two or three amino acid substitutions, deletions and/or insertions, preferably one, two or three amino acid substitutions as listed in Table 2.

TABLE 2

Sets of light chain CDR sequences suitable for use in the antibodies or fragments thereof of the present invention

| Symbol of light chain set | CDR3 sequence | CDR2 sequence | CDR1 sequence |
|---|---|---|---|
| I | SEQ ID NO: 19 | SEQ ID NO: 18 | SEQ ID NO: 17 |
| II | SEQ ID NO: 19 | SEQ ID NO: 18 | SEQ ID NO: 23 |
| III | SEQ ID NO: 19 | SEQ ID NO: 24 | SEQ ID NO: 23 |
| IV | SEQ ID NO: 19 | SEQ ID NO: 24 | SEQ ID NO: 17 |
| V | SEQ ID NO: 25 | SEQ ID NO: 18 | SEQ ID NO: 17 |
| VI | SEQ ID NO: 25 | SEQ ID NO: 24 | SEQ ID NO: 17 |
| VII | SEQ ID NO: 25 | SEQ ID NO: 24 | SEQ ID NO: 23 |
| VIII | SEQ ID NO: 25 | SEQ ID NO: 18 | SEQ ID NO: 23 |
| IX | SEQ ID NO: 19 | SEQ ID NO: 18 | SEQ ID NO: 29 |
| X | SEQ ID NO: 19 | SEQ ID NO: 30 | SEQ ID NO: 29 |
| XI | SEQ ID NO: 19 | SEQ ID NO: 30 | SEQ ID NO: 17 |
| XII | SEQ ID NO: 25 | SEQ ID NO: 30 | SEQ ID NO: 29 |
| XIII | SEQ ID NO: 25 | SEQ ID NO: 24 | SEQ ID NO: 29 |
| XIV | SEQ ID NO: 25 | SEQ ID NO: 30 | SEQ ID NO: 23 |
| XV | SEQ ID NO: 19 | SEQ ID NO: 24 | SEQ ID NO: 29 |
| XVI | SEQ ID NO: 25 | SEQ ID NO: 18 | SEQ ID NO: 29 |
| XVII | SEQ ID NO: 19 | SEQ ID NO: 30 | SEQ ID NO: 23 |
| XVIII | SEQ ID NO: 25 | SEQ ID NO: 30 | SEQ ID NO: 17 |

In a preferred embodiment of the antibody of the invention or of antigen-binding fragments thereof it comprises one of the heavy CDR sets A-R listed above in Table 1 and one of the light chain CDR sets I-XVIII listed above in Table 2, i.e. one of the following combinations of sets: A-I, A-II, A-III, A-IV, A-V, A-VI, A-VII, A-VIII, A-IX, A-X, A-XI, A-XII, A-XIII, A-XIV, A-XV, A-XVI, A-XVII, A-XVIII, B-I, B-II, B-III, B-IV, B-V, B-VI, B-VII, B-VIII, B-IX, B-X, B-XI, B-XII, B-XIII, B-XIV, B-XV, B-XVI, B-XVII, B-XVIII, C-I, C-II, C-III, C-IV, C-V, C-VI, C-VII, C-VIII, C-IX, C-X, C-XI, C-XII, C-XIII, C-XIV, C-XV, C-XVI, C-XVII, C-XVIII, D-I, D-II, D-III, D-IV, D-V, D-VI, D-VII, D-VIII, D-IX, D-X, D-XI, D-XII, D-XIII, D-XIV, D-XV, D-XVI, D-XVII, D-XVIII, E-I, E-II, E-III, E-IV, E-V, E-VI, E-VII, E-VIII, E-IX, E-X, E-XI, E-XII, E-XIII, E-XIV, E-XV, E-XVI, E-XVII, E-XVIII, F-I, F-II, F-III, F-IV, F-V, F-VI, F-VII, F-VIII, F-IX, F-X, F-XI, F-XII, F-XIII, F-XIV, F-XV, F-XVI, F-XVII, F-XVIII, G-I, G-IT, G-III, G-IV, G-V, G-VI, G-VII, G-VIII, G-IX, G-X, G-XI, G-XII, G-XIII, G-XIV, G-XV, G-XVI, G-XVII, G-XVIII, H-I, H-TI, H-III, H-IV, H-V, H-VI, H-VII, H-VIII, H-IX, H-X, H-XI, H-XII, H-XIII, H-XIV, H-XV, H-XVI, H-XVII, H-XVIII, I-I, I-II, I-III, I-IV, I-V, I-VI, I-VII, I-VIII, I-IX, I-X, I-XI, I-XII, I-XIII, I-XIV, I-XV, I-XVI, I-XVII, I-XVIII, J-I, J-II, J-III, J-IV, J-V, J-VI, J-VII, J-VIII, J-IX, J-X, J-XI, J-XII, J-XIII, J-XIV, J-XV, J-XVI, J-XVII, J-XVIII, K-I, K-II, K-III, K-IV, K-V, K-VI, K-VII, K-VIII, K-IX, K-X, K-XI, K-XII, K-XIII, K-XIV, K-XV, K-XVI, K-XVII, K-XVIII, L-I, L-II, L-III, L-IV, L-V, L-VI, L-VII, L-VIII, L-IX, L-X, L-XI, L-XII, L-XIII, L-XIV, L-XV, L-XVI, L-XVII, L-XVIII, M-I, M-II, M-III, M-TV, M-V, M-VI, M-VII, M-VIII, M-IX, M-X, M-XI, M-XII, M-XIII, M-XIV, M-XV, M-XVI, M-XVII, M-XVIII, N-T, N-II, N-III, N-IV, N-V, N-VI, N-VII, N-VIII, N-IX, N-X, N-XI, N-XII, N-XIII, N-XIV, N-XV, N-XVI, N-XVII, N-XVIII, O-I, O-II, O-III, O-IV, O-V, O-VI, O-VII, O-VIII, O-IX, O-X, O-XI, O-XII, O-XIII, O-XIV, O-XV, O-XVI, O-XVII, O-XVIII, P-I, P-II, P-III, P-IV, P-V, P-VI, P-VII, P-VIII, P-IX, P-X, P-XI, P-XII, P-XIII, P-XIV, P-XV, P-XVI, P-XVII, P-XVIII, Q-I, Q-TI, Q-III, Q-IV, Q-V, Q-VI, Q-VII, Q-VIII, Q-IX, Q-X, Q-XI, Q-XII, Q-XIII, Q-XIV, Q-XV, Q-XVI, Q-XVII, Q-XVIII, R-I, R-II, R-III, R-IV, R-V, R-VI, R-VII, R-VIII, R-IX, R-X, R-XI, R-XII, R-XIII, R-XIV, R-XV, R-XVI, R-XVII, R-XVIII, preferably the combinations are as follows A-I, G-VII, L-XII.

wherein each heavy chain CDR3 sequence comprises one or two amino acid substitutions, deletions and/or insertions, preferably one or two amino acid substitutions as listed above in Table 1; wherein each heavy chain CDR2 sequence comprises one or two amino acid substitutions, deletions and/or insertions, preferably one or two amino acid substitutions as listed above in Table 1; wherein each heavy chain CDR1 sequence comprises one, two or three amino acid substitutions, deletions and/or insertions, preferably one, two or three amino acid substitutions as listed above in Table 1; wherein each light chain CDR3 sequence comprises one or two amino acid substitutions, deletions and/or insertions, preferably one or two amino acid substitutions as listed above in Table 2; wherein each light chain CDR2 sequence comprises one or two amino acid substitutions, deletions and/or insertions, preferably one or two amino acid substitutions as listed above in Table 2; wherein each light chain CDR1 sequence comprises one, two or three amino acid substitutions, deletions and/or insertions, preferably one, two or three amino acid substitutions as listed above in Table 2.

In preferred embodiments of the fourth aspect, the antibody or antigen-binding fragment thereof comprising one or more CDRs, a set of CDRs or a combination of sets of CDRs as described herein comprises said CDRs in a human antibody framework.

In a preferred embodiment of the fourth aspect the antibody is a polyclonal or monoclonal antibody.

In a further preferred embodiment of fourth aspect the antibody is a human or humanized antibody.

In a further embodiment of the fourth aspect the present invention is directed to an isolated monoclonal antibody, wherein the antibody binding portion comprises a light chain comprising an amino acid sequence at least 80%, preferably at least 85%, preferably at least 90%, more preferably at least 91%, more preferably at least 92%, more preferably at least 93%, more preferably at least 94%, more preferably at least 95%, even more preferably at least 96%, even more preferably at least 97%, even more preferably at least 98%, even more preferably at least 99% or most preferably at least 100% identical to the light chain variable region amino acid sequence set forth in SEQ ID NO: 7, SEQ ID NO: 11, or SEQ ID NO: 13.

In a further preferred embodiment the antibody or antibody binding portion comprises a heavy chain comprising an amino acid sequence at least 80%, preferably at least 85%, preferably at least 90%, more preferably at least 91%, more preferably at least 92%, more preferably at least 93%, more preferably at least 94%, more preferably at least 95%, even more preferably at least 96%, even more preferably at least 97%, even more preferably at least 98%, even more preferably at least 99% or most preferably at least 100% identical to the heavy chain variable region amino acid sequence set forth in SEQ ID NO: 8, SEQ ID NO: 12, or SEQ ID NO: 14.

In a fifth aspect, the present invention is further directed to a pharmaceutical composition, which comprises a nucleic acid of the invention, an expression vector or the invention or an antibody of the invention and a pharmaceutically acceptable carrier or excipient.

As used herein, the expressions "is for administration" and "is to be administered" have the same meaning as "is prepared to be administered". In other words, the statement that an active compound "is for administration" has to be understood in that said active compound has been formulated and made up into doses so that said active compound is in a state capable of exerting its therapeutic activity.

The terms "therapeutically effective amount" or "therapeutic amount" are intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990)

Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

The term "acceptable carrier or excipient" as used herein, refers to a diluent, adjuvant, excipient, or vehicle with which the therapeutic agent is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper In a preferred embodiment of pharmaceutical further comprises an anti-neoplastic agent as outlined above.

In a preferred embodiment of the pharmaceutical composition further comprises an antibody against oncogenic or stromal proteins. Such antibodies are known in the art.

In a sixth aspect the present invention is directed to a kit, which comprises an isolated nucleic acid fragment or a vector in a container and an instruction for using the isolated nucleic acid fragment in preventing, treating or delaying a neoplasm.

The present invention among other things also relates to:
1. A nucleic acid comprising a nucleotide sequence encoding a mammal ErbB3 H584F mutant protein said protein comprising a sequence of amino acid as set forth in SEQ ID NO: 2 or a functional fragment thereof, wherein one or more of the nucleotide codons encoding the protein that occur with low frequency in proteins expressed in mammal cells have been replaced with nucleotide codons present on nucleic acids encoding highly expressed proteins.
2. An expression vector comprising the nucleic acid of item 1 operatively linked to a promoter or to a regulatory transcriptional element, belonging preferentially but not exclusively to the following classes: bacterial plasmid, adenovirus, poxvirus, vaccinia, fowlpox, herpes, adeno-associated virus (AAV), alphavirus, lentivirus, lambda phage, lymphocytic choriomeningitis virus, *Listeria* sp, *Salmonella* sp.
3. A method for preventing, treating or delaying neoplams in a mammal, which method comprises administering to a mammal, to which such preventiom treatment or delay is needed or desirable a nucleic acid of item 1 encoding Erbb3 H584F mutant protein, or a functional fragment thereof, whereby an immune response is generated against said neoplasm and said neoplasm is prevented, treated or delayed.
4. The method of item 3, wherein the mammal is a human, mouse, rat or dog.
5. The method of item 3, wherein the nucleic acid encoding Erbb3 H584F and its extracellular domain comprises a nucleic acid set forth in SEQ ID NO: 1 and SEQ ID NO: 3.
6. The method of item 3, further comprising administering the nucleic acid by DNA electroporation in the muscle or to the neoplasm in situ.

7. The method of item 3, further comprising administering an immune response potentiator to the mammal.
8. The method of item 3, wherein the nucleic acid is co-administered with a pharmaceutically acceptable carrier or excipient.
9. The method of item 3, wherein the nucleic acid is co-administered in combination with a known therapeuticanti-neoplasm regimen.
10. The method of item 9, wherein the anti-neoplasm agent is selected from the group consisting of an anti-angiogenic agent, an alkylating agent, an antimetabolite, a natural product, a platinum coordination complex, an anthracenedione, a substituted urea, a methylhydrazine derivative, an adrenocortical suppressant, a hormone, an antagonist, an oncogene inhibitor, a tumor suppressor gene or protein, a therapeutic antibody and an anti-oncogene oligonucleotide.
11. The method of item 3, wherein the neoplasm to be prevented treated or delayed is selected from the group consisting of adrenal gland, anus, auditory nerve, bile ducts, bladder, bone, brain, breast, central nervous system, cervix, colon, ear, endometrium, esophagus, eye, eyelids, fallopian tube, gastrointestinal tract, head and neck, heart, kidney, larynx, liver, lung, mandible, mandibular condyle, mouth, nasopharinx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve and vulva neoplasm.
12. An antibody generated with the method of item 3, which antibody binds to an epitope in an extracellular domain of the ErbB3 protein, or a functional fragment thereof and exhibits one or more of the following properties:
   i. Inhibition of heregulin, epiregulin, betacellulin, epigen or biregulin-mediated signalling through ErbB3;
   ii. Inhibition of proliferation of cells expressing ErbB3;
   iii. The ability to decrease levels of ErbB3 on cell surfaces;
   iv. Inhibition of VEGF secretion of cells expressing ErbB3;
   v. Inhibition of the migration of cells expressing ErbB3; and
   vi. Inhibition of spheroid growth of cells expressing ErbB3.
13. The antibody of item 12, which is a polyclonal or monoclonal antibody.
14. The antibody of item 12, which is a human or humanized antibody.
15. An isolated monoclonal antibody of item 14, wherein the antibody binding portion comprises a light chain comprising an amino acid sequence at least 80% identical to the light chain variable region amino acid sequence set forth in SEQ ID NO: 7, SEQ ID NO: 11, SEQ ID NO: 13.
16. An isolated monoclonal antibody of item 12, wherein the antibody binding portion comprises a heavy chain comprising an amino acid sequence at least 80% identical to the heavy chain variable region amino acid sequence set forth in SEQ ID NO: 8, SEQ ID NO: 12, SEQ ID NO: 14.
17. A pharmaceutical composition, which pharmaceutical composition comprises an antibody of item 12 and a pharmaceutically acceptable carrier or excipient.
18. The pharmaceutical composition of item 17, which further comprises an antineoplasm agent.
19. The pharmaceutical composition of item 17, which further comprises an antibody against oncogenic or stromal proteins.
20. A kit, which kit comprises an isolated nucleic acid fragment of item 1 in a container and an instruction for using the isolated nucleic acid fragment in preventing, treating or delaying a neoplasm.

FIGURE LEGENDS

FIG. 1: Panel A depicts the structure of the plasmid pTK1-A-HER3-H584F-FL$_{opt}$, which encodes a codon optimized version of full length human HER3 carrying a mutation at position 584 from His to Phe. Panel B depicts the structure of the plasmid pTK1-A-HER3-H584F-ECD$_{opt}$, which encodes a codon optimized C-terminally truncated form of human HER3 comprising the extracellular domain. Panel C depicts the results of an ELISA assay of sera of BALB/c mice (8 animals) immunized with the vaccine. A significant reactivity against recombinant HER3 was observed for all sera.

Figure 2:
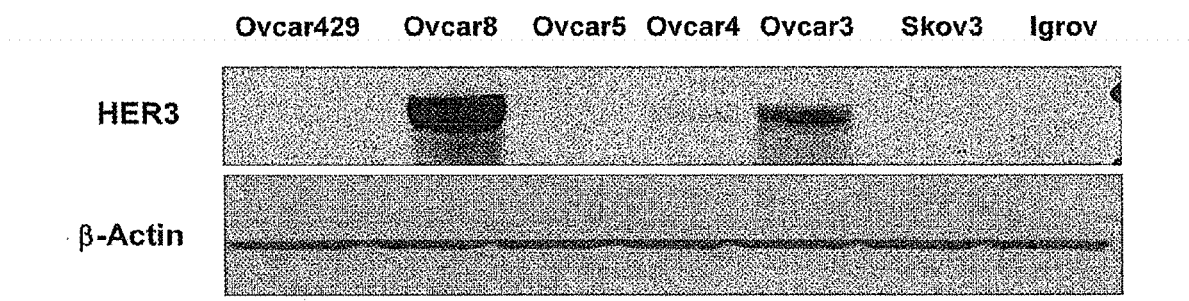
Figure 2:
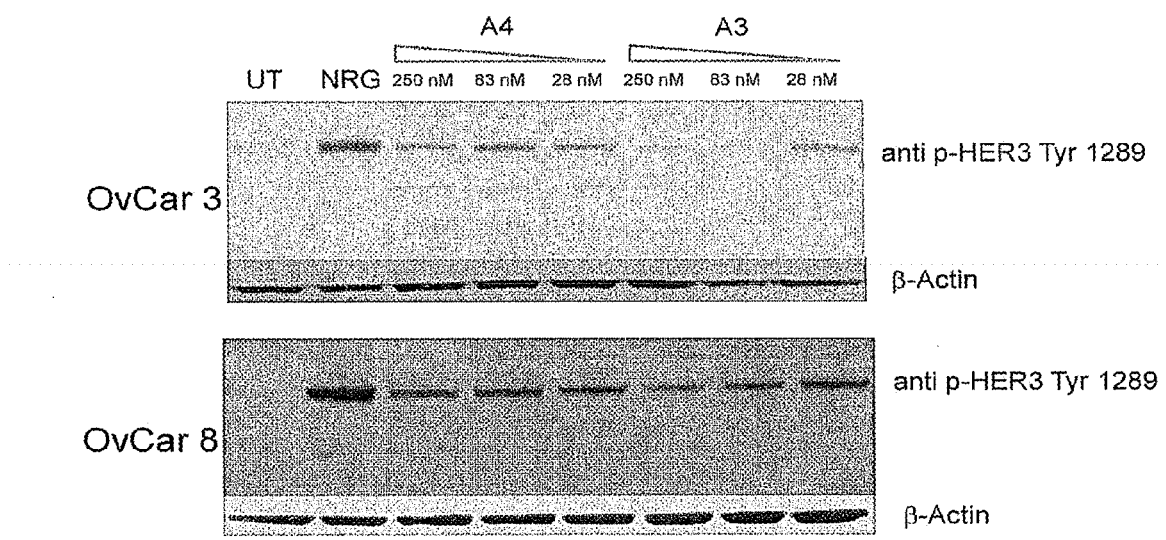

FIG. 2: Panel A depicts a Western blot of cell extracts of various cancerous cell lines with an anti-HER3 antibody. It is evident that the OvCar 3 and OvCar8 cell lines have the highest levels of HER3 expression. Panel B depicts a Western blot of cell extracts of OvCar 3 and OvCar8, wherein phosphorylated HER3 is detected by an anti-pHER3-Tyr 1298 phosphorylation specific antibody in the presence of different amounts of HER3-specific antibodies A3 and A4 of the invention.

Figure 3:
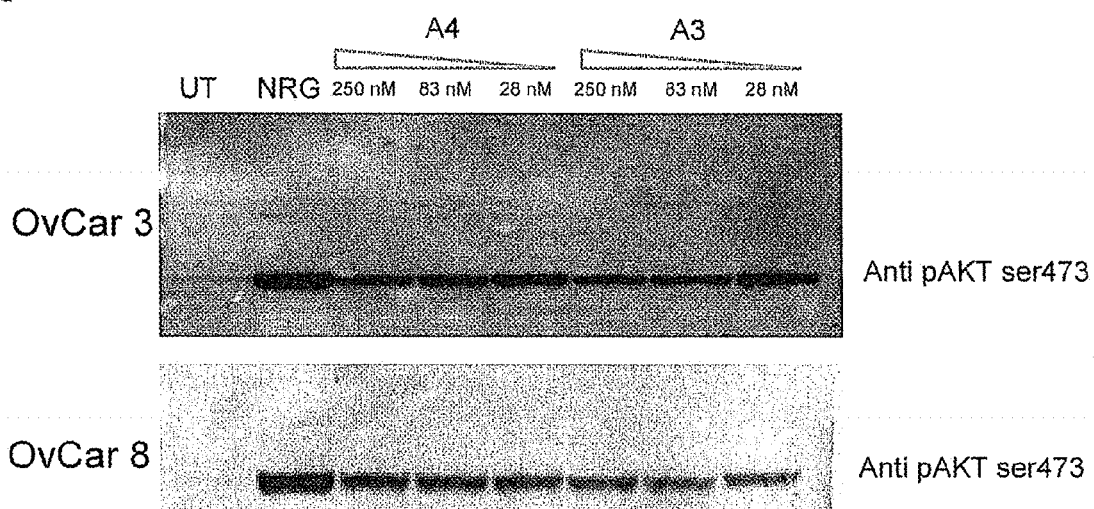
Figure 3:
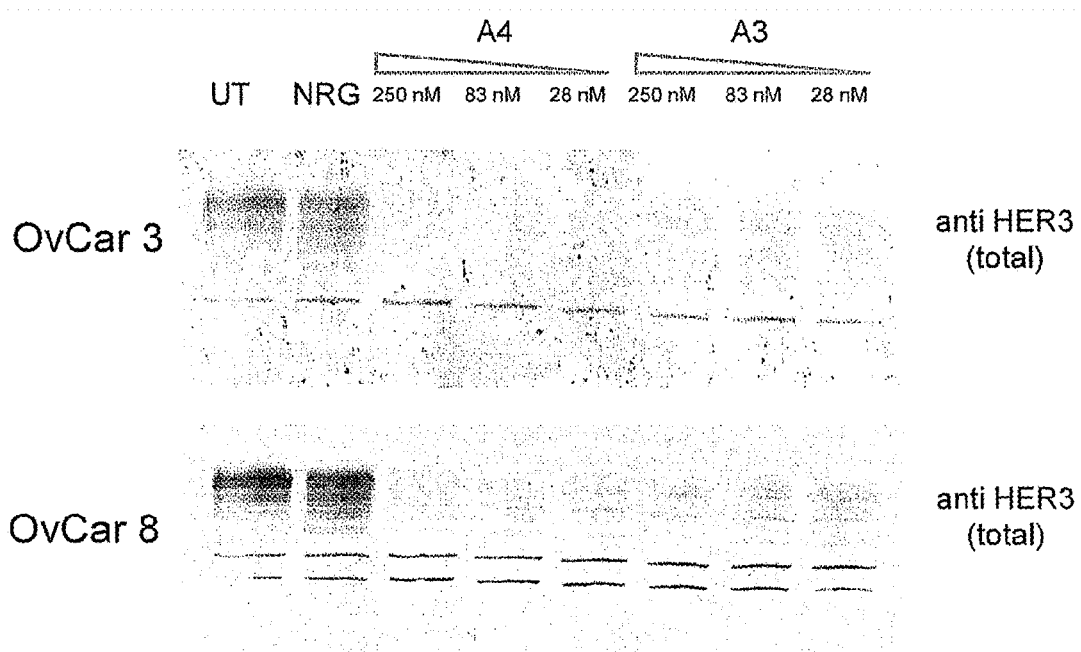

FIG. 3: Panel A depicts a Western blot of cell extracts of OvCar 3 and OvCar8, wherein phosphorylated AKT is detected by an anti-pAKT Ser 473 phosphorylation specific antibody in the presence of different amounts of HER3-specific antibodies A3 and A4 of the invention. Panel B depicts a Western blot of OvCar 3 and OvCar8 cell lines with a HER3 specific antibody in the presence of different amounts of HER3-specific antibodies A3 and A4 of the invention.

Figure 4:
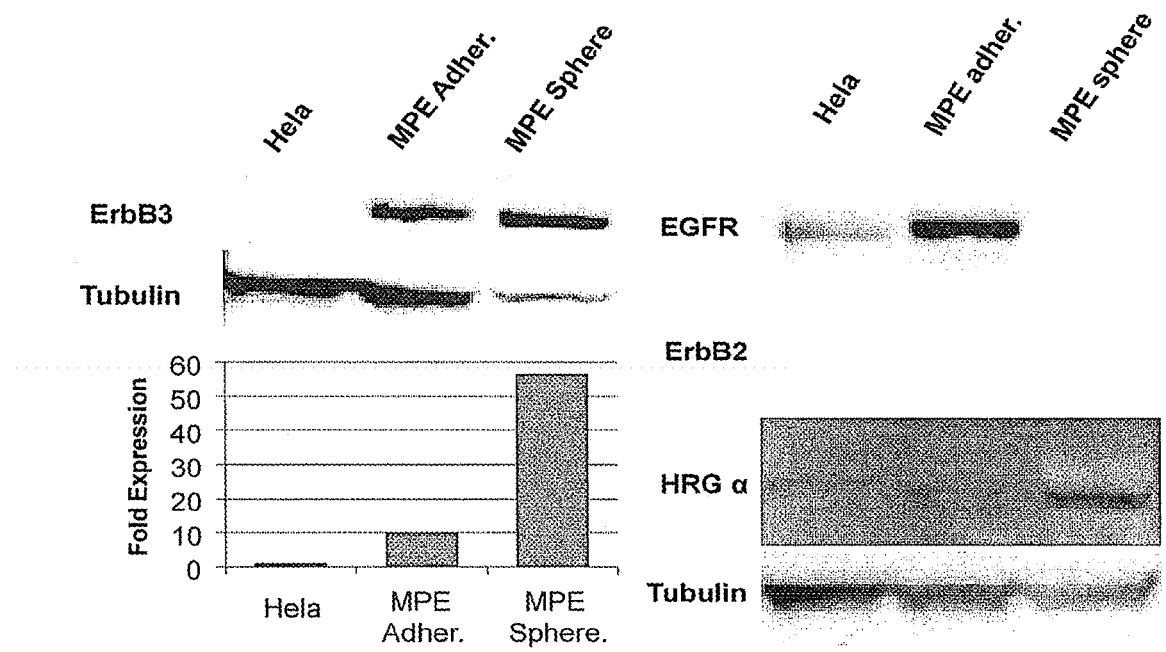
Figure 4:
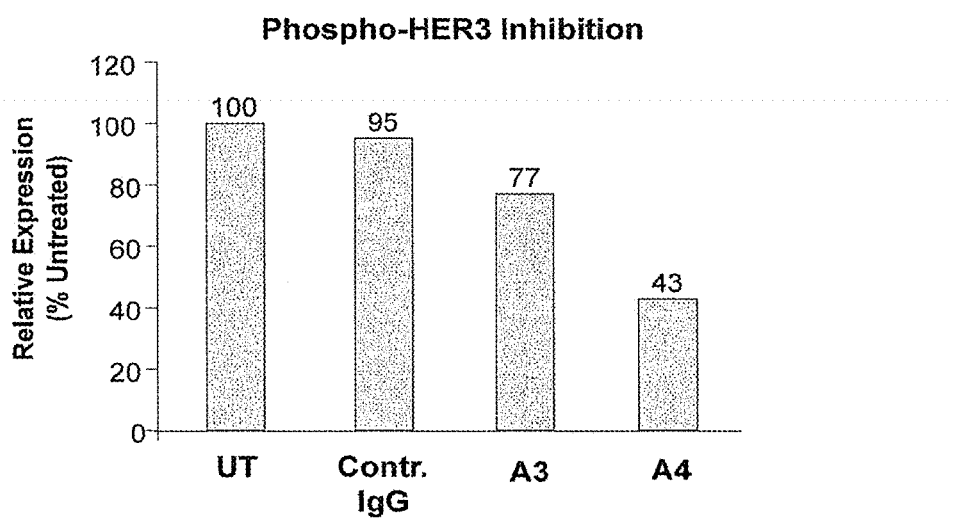

FIG. 4: Panel A depicts a Western blot of cell extracts of HeLa cells, adherently growing primary cell cultures established from Malignant Pleural Effusions (MPEs) and spherically growing MPEs with five different antibodies directed against EGFR, ErbB2, HRG, Tubulin and ErbB3/Her2. Panel B depicts the inhibition of phosphor-HER3 expression in the control (UT), by an unspecific IgG (Contr. IgG), with the HER3 specific antibodies of the invention A3 and A4 (A3 and A4, respectively).

Figure 5:
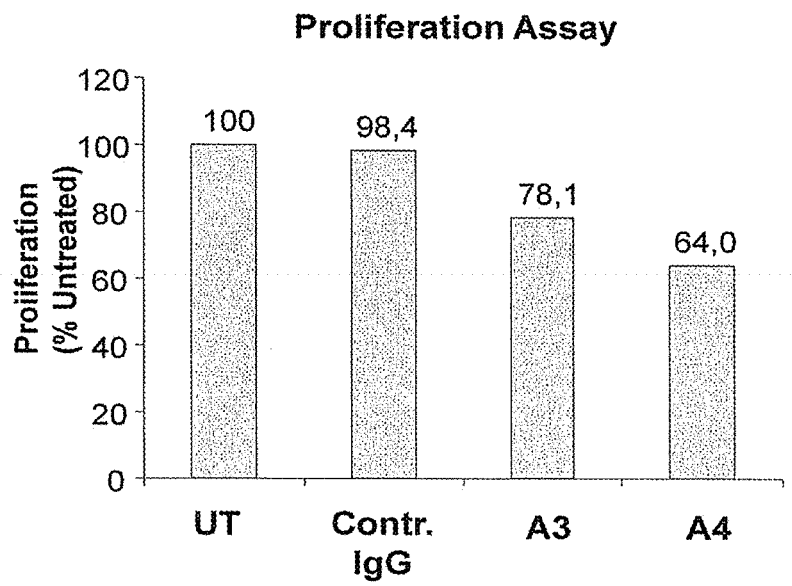
Figure 5:
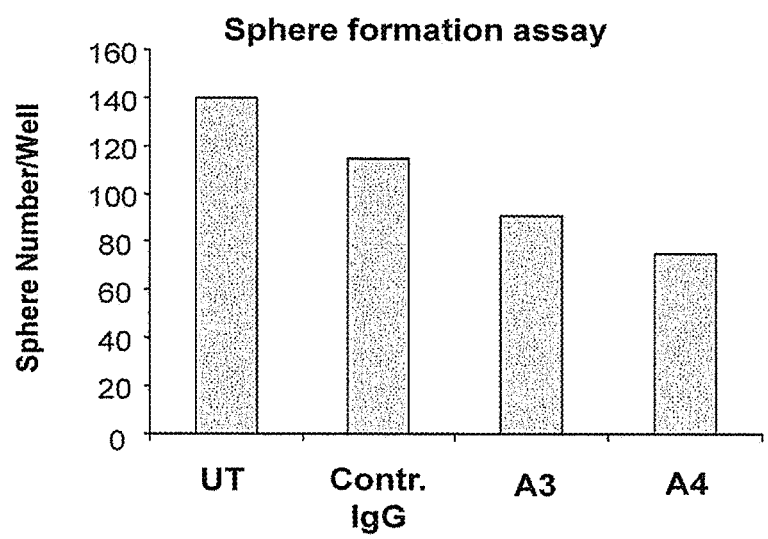

FIG. 5: Panel A depicts the results of an assay evaluating tumor cell proliferation inhibition by antibodies A3 and A4. Panel B depicts the results of an assay evaluating inhibition of spherer formation of MPEs by antibodies of the invention A3 and A4.

Figure 6:
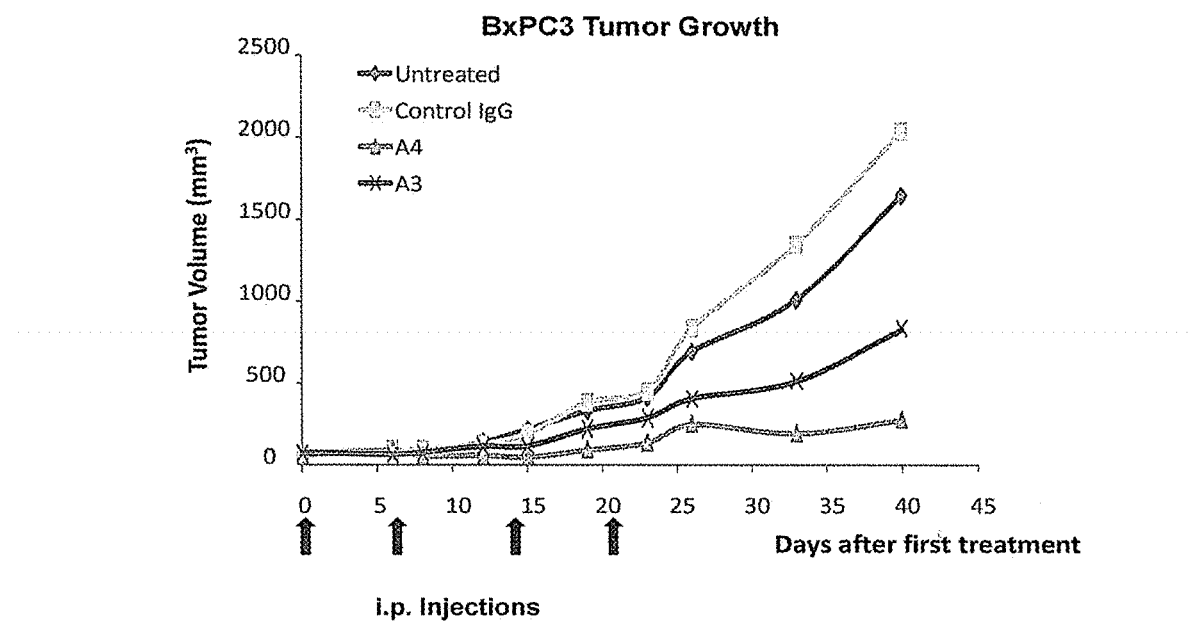
Figure 6:
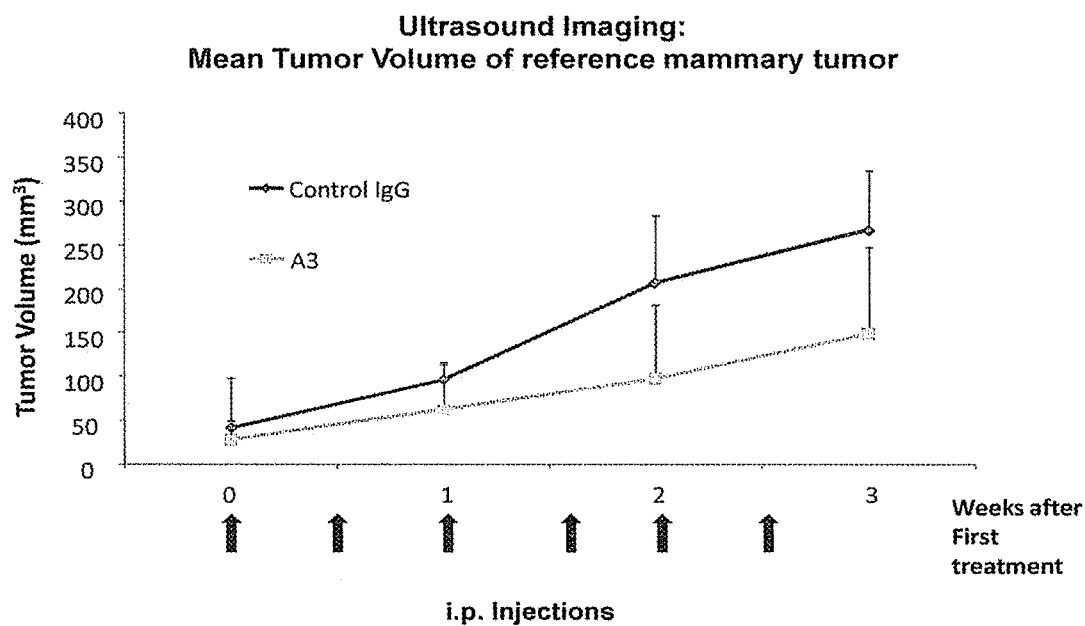

FIG. 6: Panel A depicts the results of an experiment, wherein the inhibitory activity of HER3 specific A3 and A4 antibodies of the invention on tumors is evaluated that are formed by implantation of cells from the human tumor cell line BxPC3 in CD1 nude mice. Panel B depicts the results of an experiment, wherein the efficacy of anti-HER3 antibodies of the invention A3 and A4 in the BALB/neuT model is evaluated.

Figure 7:
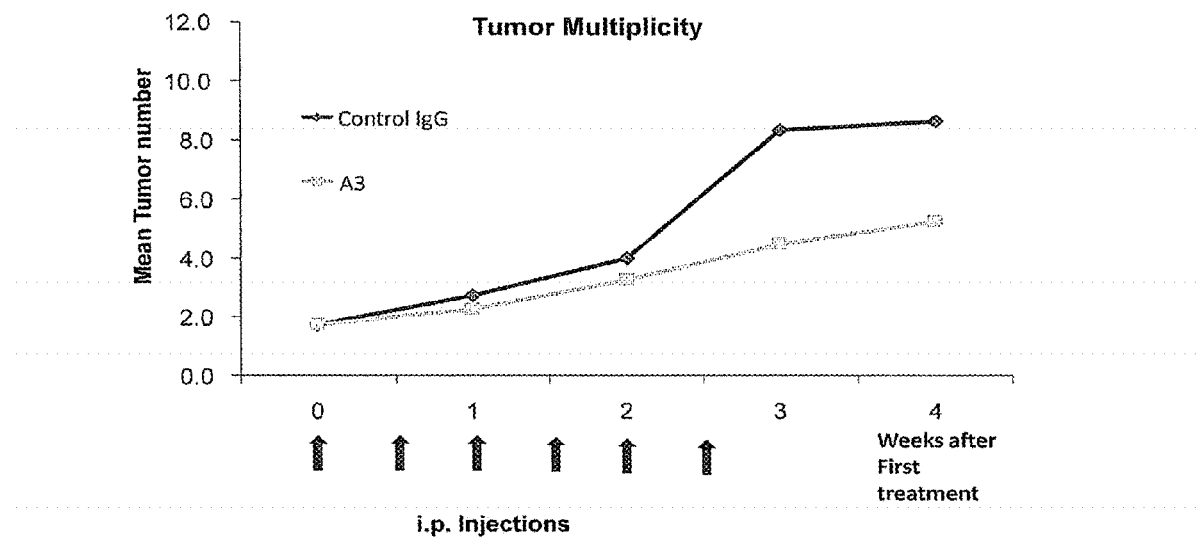
Figure 7:
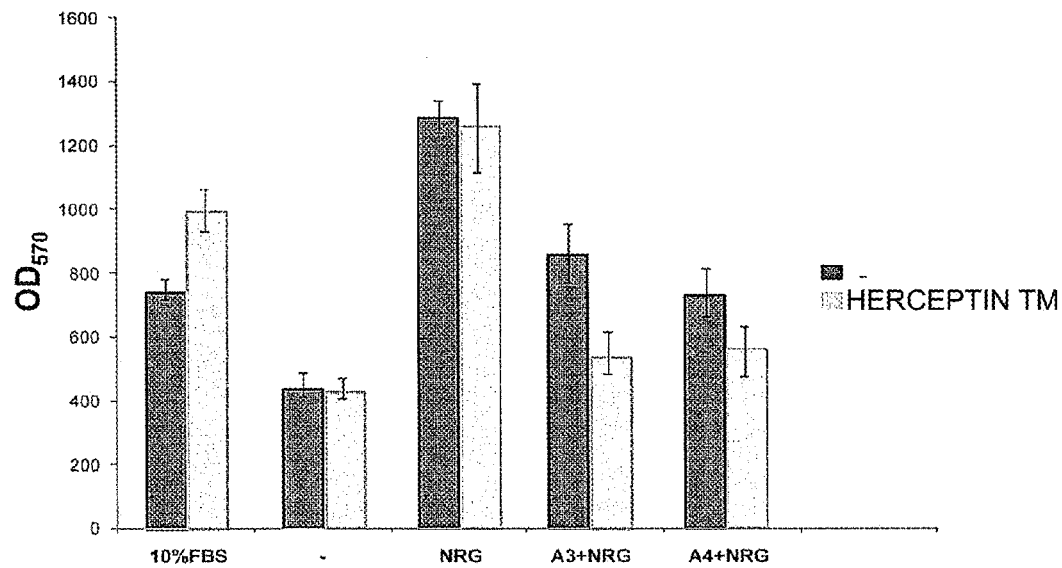

FIG. 7: Panel A depicts the results of an experiment evaluating the effect of A3 and A4 on tumor multiplicity in the BALB/neuT model over time. Panel B depicts the results of an experiment evaluating the influence of 10% serum, no serum, the presence of NRG alone or of antibodies A3 or A4 in each case with or without Her2 specific antibody HERCEPTIN™ (trastuzumab).

Figure 8:
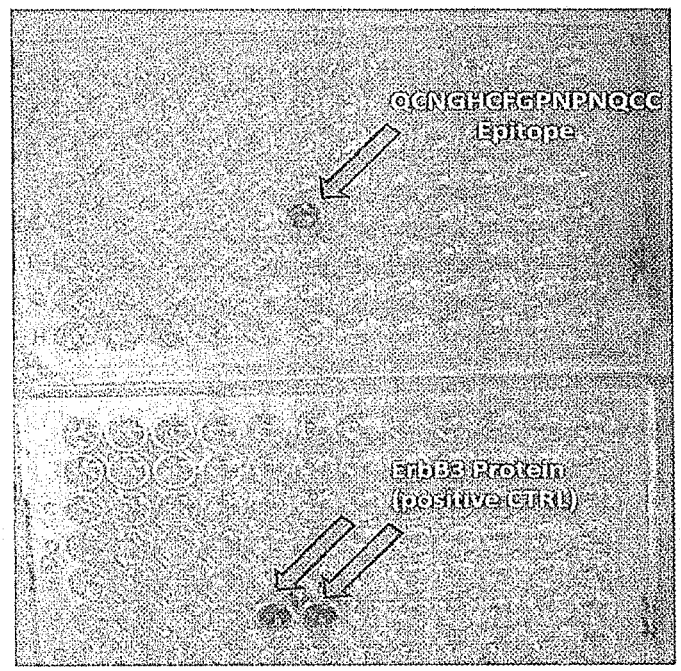
Figure 8:
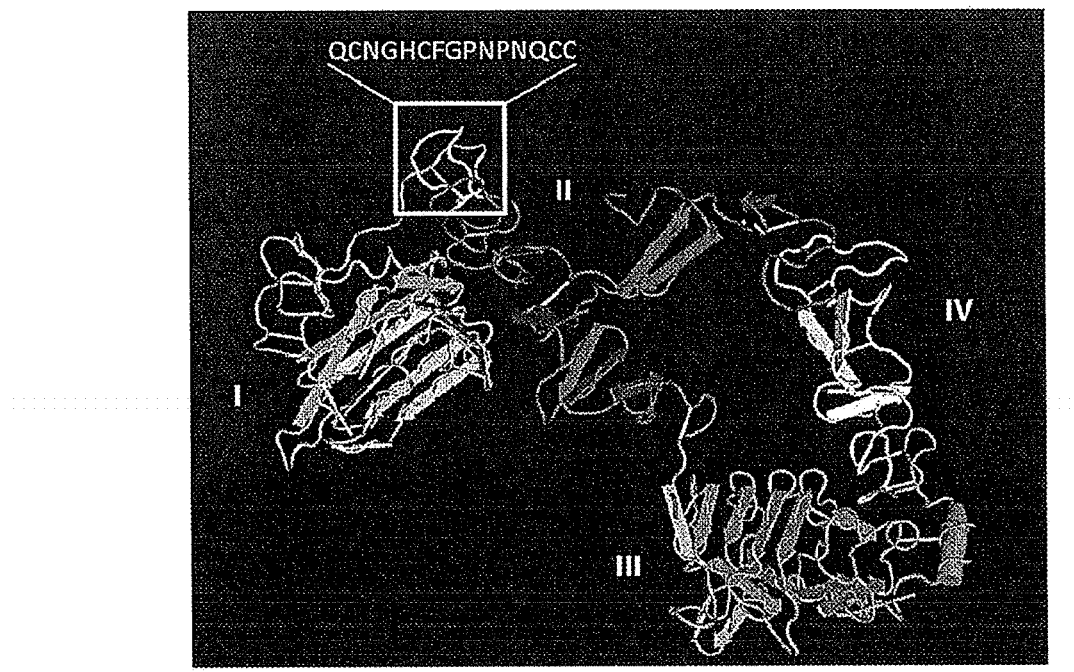

FIG. 8: Panel A depicts the results of the epitope mapping assay of A3 antibody. Wells containing the epitope QCNGH- CFGPNPNQCC (SEQ ID NO: 68) and positive controls with human ErbB3 recombinant protein are shown by arrows. Panel B depicts the position of the epitope (in yellow) within the crystal structure of ErbB3. Domains I, II, III and IV are indicated with different color codes.

Figure 9:
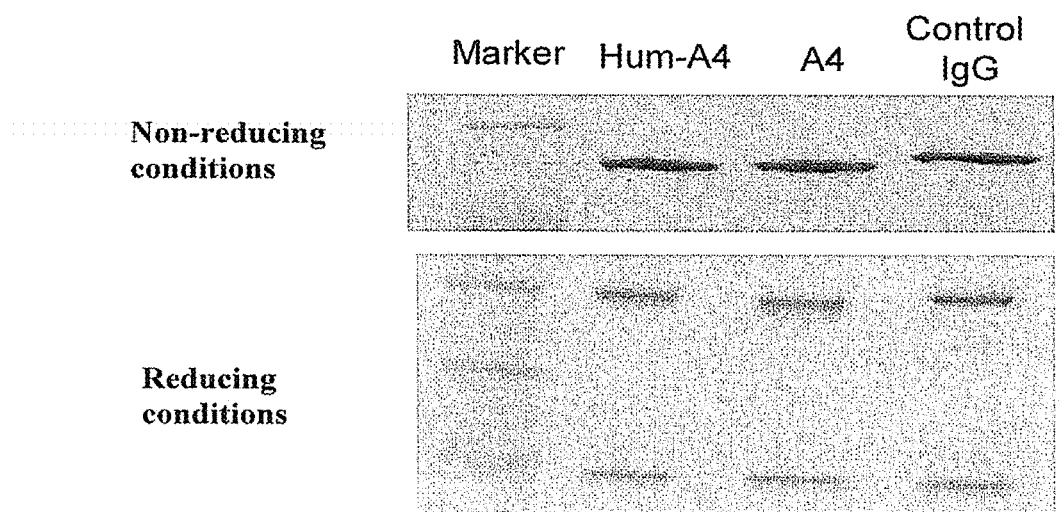
Figure 9:
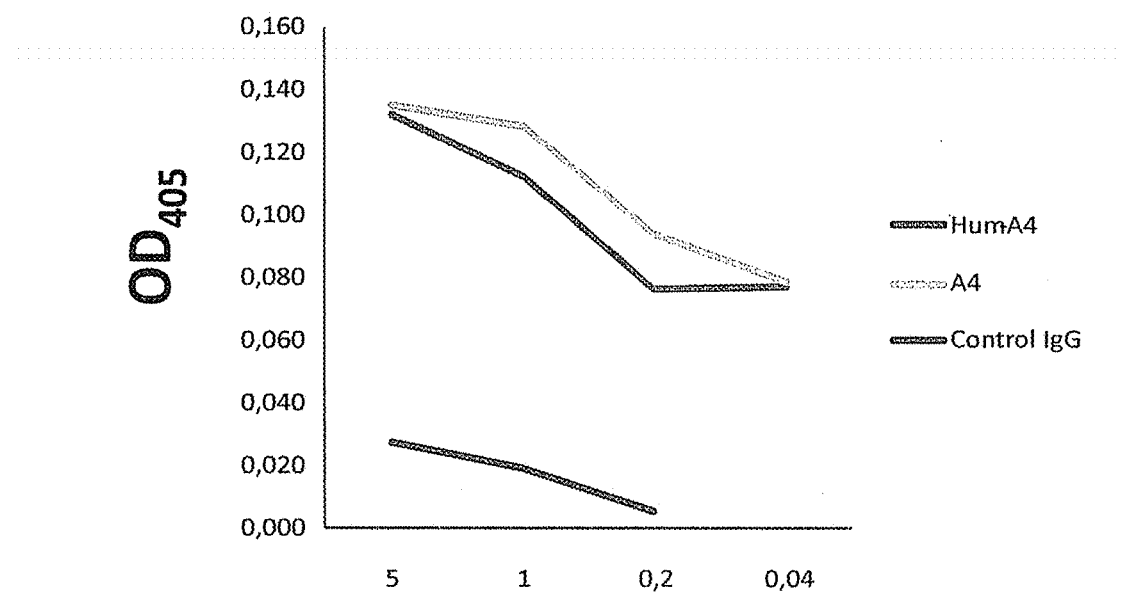

FIG. 9: Panel A depicts a quantification of humanized A4, A4 and Control IgG immunoglobulins in a Coomassie stained SDS gels run under denaturing or non-denaturing conditions. Panel B depicts the results of an experiment comparing the specificity of binding of humanized A4 (humA4) and murine A4 (A4) to human HER3. Control IgG is an unspecific IgG control.

FIG. 10: Depicts the amino acid sequences of the Variable heavy and light chain domains of A3, A4 and humanized A4. In each case the amino acids constituting the complementarity determining region (CDR) 1, 2 or 3 are indicated by bold print.

EXAMPLES

Example 1

A Genetic Vaccine Against a Genetic Variant of HER3

In order to obtain a strong immune response against HER3 and in particular in order to induce neutralizing antagonistic antibodies anti-HER3 in the organism, a genetic vaccination approach has been adopted, which is based on DNA electroporation in skeletal muscles (DNA-EP, ref 21). This technology allows both the use of appropriately engineered modified variants of the antigen of interest, and allows its endogenous expression in the muscle and in antigen presenting cells. A plasmid vector has been utilized which carries a modified HER3 cDNA whose codons have been optimized for their presence in the coding region of proteins highly expressed in human cells. This modified cDNA also expresses a mutant form of the receptor with a single amino acid substitution H584F described in SEQ ID:1. The amino acid sequence of the protein is depicted in SEQ ID:2. In the absence of the ligand, HER3 is present on the cell surface in a closed conformation which is tethered together by intramolecular bonds. When bound to its ligand, HER3 adopts an extended conformation which exposes receptor domains responsible for the heterodimerization with other ErbB receptors and other RTK partners. Since mutant H584F is constantly held in an open conformation [22], also in the absence of the ligand, we postulated that immunizations with this variant should increase the probability of obtaining neutralizing antibodies.

The immunization protocol consisted of 2 injections in the quadriceps muscle with 50 µg of plasmid pTK1-A-HER3-H584F-FL$_{opt}$ (FIG. 1A) followed by 2 injections with 50 µg of plasmid pTK1-A-HER3-H584F-ECD$_{opt}$ (FIG. 1B), carrying the cDNA coding for the ECD domain with the mutation H584F (nucleotide sequence in SEQ ID:3, amino acid sequence in SEQ ID:4). DNA injections were spaced 2 weeks from one another. DNA was formulated in Phosphate Buffered Saline (PBS) at a concentration of 1 mg/ml. Antigen expression was driven by cytomegalovirus promoter (CMV) upstream of the intron A and the HER3 cDNA was followed by the bovine Growth Hormone (bGH) polyadenylation signal. DNA electroporation in vivo was carried out with a BTX electroporator, model BTX 830, and plate electrodes at a distance of 0.5 cm (BTX, Harward apparatus) using the following electrical conditions in Low voltage: 2 pulses of 60 msec at 100V, with 250 msec pause between pulses. All BALB/c immunized mice (8 animals) responded to the vaccine and their sera showed a significant reactivity against recombinant HER3 in an ELISA assay (FIG. 1C).

Two weeks after the fourth and last immunization, mice were euthanized and spleens and lymphnodes removed. After a standard fusion protocol with murine myeloma cells as described in Harlow et al, "Antibodies: a laboratory manual", more than 100 hybridoma clones were isolated by limiting dilution and their supernatant tested again for binding to recombinant HER3 in vitro.

Example 2

Biochemical and Functional Analysis

Among the hybridomas described above, two antibodies, A3 and A4, were further selected for a biochemical and functional characterization. In particular, the following assays have been performed:

Bioacore analysis. Affinity for HER3 and $k_{on}/k_{off}$ were determined by Surface Plasmon Resonance using a Biacore T100 instrument. A biosensor chip CM5 (GE Healthcare) was covalently bound to an anti-Fc (8000 RU) and then treated with antibodies at different concentrations (<1000 RU). Recombinant protein HER3-ECD-Fc (RnD Systems) in HBS-EP buffer at the analyte concentration 1:1 was injected for 2 minutes at 30 µl/min, followed by a 10 minutes dissociation phase.

Cross-reactivity with mouse HER3 receptor and with other human ErbB receptors. In order to assess potential cross-reactivity with other ErbB receptors, cells negative for ErbB receptors expression (CHO) were transiently transfected with expression vectors (pCDNA3) for human or mouse HER3, HER1/EGFR, HER2 or HER4. 5×10$^5$ cells were transfected in 6 cm plates with 5 µg of plasmid DNA using Lipofectamine 2000 (Gibco). After 48 hours, cells were trypsinized, washed with culture medium and incubated with 10 µg/ml of each antibody in FACS buffer (PBS, 1% FBS). After a wash in FACS buffer, an anti-mouse IgG conjugated with Phycoerythrin (PE, Becton Dickinson) was added and cells were analyzed by a FACSCalibur (Becton Dickinson).

Ligand blocking assay. In order to measure the ability of antibodies to inhibit the binding of neuregulin (NRG) to HER3, competition assays with the ligand were carried out using an ELISA assay. In detail, the recombinant protein HER3-ECD-Fc was bound to Nunc Maxisorp plastic plates over night at the concentration of 1 µg/ml in PBS at 4° C. Anti-HER3 antibodies were then added for 1 hour at 37° C., followed by an incubation for 1 hour with 90 ng/100 µl/well with NRG-1β (RnD Systems, final concentration 10 nM). After 2 washes with PBS, 0.05% Tween20, the signal was measured by incubation with a biotinylated goat anti-NRG-1β antibody (RnD Systems) and Streptavidin conjugated with peroxidase and utilizing an HRP substrate (Pierce). Data were acquired with an ELISA reader at 450 nm.

HER3 and Akt Activation/Phosphorylation assays. ELISA assays have been performed to check whether anti-HER3 antibodies were able to block NRG-mediated HER3 activation. MCF-7 cells, were grown to 70% confluence in 6 cm plates and then starved O/N in culture medium (RPMI) with 0.1% BSA. Cells were then incubated for 1 hour with anti-HER3 antibodies and then treated with 3.3 nM (100 ng/ml) NRG1β in medium comprising 0.1% BSA for 20 min at 37° C. Cell extracts were prepared and ELISA assays performed according to the instructions of the kit DUOset IC Human Phospho-ErbB3 and Human Phospho-Akt (RnD Systems). Percent inhibition was calculated using as reference an unrelated IgG as negative control.

Receptor Internalization/Degradation assays. Disappearance of the HER3 receptor from cell surface following its internalization and/or degradation interferes with intracellular signalling, and therefore with cell transformation and/or maintenance of tumorigenicity. These assays were carried out using FACS analysis. In particular, MCF-7 cells were trypsinized, resuspended in FACS buffer and counted. $1 \times 10^6$ cells in each tube were incubated with antibodies for 3 hours at 37° C. using a control isotype antibody. After a wash in FACS buffer, a further incubation with the same antibodies was executed for 30 min at 4° C., followed by an incubation with an anti-mouse IgG-PE using the same conditions. Cells were then fixed in PBS, with 10% formaldehyde and analyzed by FACSCalibur. Percent internalization was calculated using a reference IgG as negative control.

Proliferation assays. In order to assess the ability of anti-HER3 antibodies to inhibit cell proliferation induced by NRG, the following experiments were performed in vitro using MCF-7 cells. 2000 cells/well were seeded in 96 well plates in culture medium conditioned with FBS over night. Following that, cells were incubated in quadruplicates with the anti-HER3 antibodies at a concentration of 100 µg/ml in medium conditioned with 0.5% FBS for 1 hour at 37° C., and then stimulated with 30 ng/ml of NRG1β for 72 hours. The Alamar Blue (Biosource) dye was then added, and after incubation for 90 minutes, absorbance was measured with an ELISA reader at 590 nm. Percent inhibition was calculated using a reference IgG as negative control.

The following table summarizes the results obtained and the features of A3 and A4 monoclonal antibodies.

| Ab | Specificity (other HER) | Binding to murine HER3 | Biacore (Kd, nM) | NRG Ligand Blocking (nM) | Inhibition of pHER3 binding stimulation nM/Max % | pAkt Inhibition, % at 100 nM | Receptor Internalization, % | Inhibition of cell proliferation, MCF-7, % |
|---|---|---|---|---|---|---|---|---|
| A3 | Only HER3 | Yes | 7.4 ± 0.3 | 1.1 ± 0.4 | 5.0/80 | 79 ± 9.5 | 48 ± 3 | 60 ± 15 |
| A4 | Only HER3 | No | 2.4 ± 0.1 | 2.8 ± 0.4 | 7.0/78 | 69 ± 6.2 | 43 ± 5 | 92 ± 12 |

Example 3

Efficacy of Anti-HER3 Antibodies on Human Ovarian Cancer Cell Lines

HER3 expression has been reported in ovarian carcinoma [23]; hence cancer cells lines of this origin can be utilized to test the antitumor effect of anti-HER3 antibodies. In order to select the most suitable cell lines, a Western Blot was performed with a commercial anti-HER3 antibody (1B2E, Cell Signalling), using cell extracts derived from various cell lines: OvCar429, OvCar3, OvCar4, OvCar8, Skov3 and Igrov. 50 µg of each cell extract were loaded on a NuPage gel 4-12% (Invitrogen) and blotted onto nitrocellulose. After blocking for 30 minutes with PBS, 5% milk, 0.5% Tween20, the anti-HER3 antibody was added and incubated over night at 4° C. After several washes, the filter was incubated with a secondary anti-rabbit IgG conjugated with peroxidase for one hour at room temperature, washed and treated with an ECL substrate (Amersham). Results, in FIG. 2A, show that the OvCar 3 and OvCar8 cell lines have the highest levels of HER3 expression.

In order to verify the effect of A3 and A4 antibodies on signal transduction in OvCar3 and OvCar8, cells were seeded in 6 cm plates, grown to 70% confluence and starved for 20 hours in RPMI with the addition of 0.05% BSA. Antibodies A3 or A4 were added at the concentrations of 250 nM, 83 nM and 28 nM for 90 minutes. Then cells were stimulated with NRG at the concentration of 80 ng/ml for 20 minutes and protein extracts quickly prepared. A commercial anti-pHER3 and an anti-pAKT antibody (Cell Signalling) were used to study the effect on signalling transduction. FIGS. 2B and 3A, respectively, show that the inhibition of pHER3 and pAKT is dose-dependent on both cell lines. In order to verify the effect of A3 and A4 monoclonal antibodies on total HER3 in both cell, the same commercial anti-HER3 antibody described before has been utilized in Western Blots. The results show that both A3 and A4 induce a strong degradation of the receptor in these cell lines (FIG. 3B).

Example 4

Expression of ErbB Receptor Members in Spheroids from Primary Lung Cancer Cells.

It has been recently shown that Malignant Pleural Effusions (MPEs) are one of the best sources of primary lung tumor cells, because that can easily be propagated in vitro and in vivo and reproduce the natural heterogeneity of tumors [24]. The preparation of primary cultures from MPEs has been performed from effusions obtained from patients with lung adenocarcinomas. In order to collect cells, the pleural fluid has been centrifuged for 10 min at 1500 rpm using a centrifuge Heraeus Sepatech Omnifuge 2.0 RS. The cell pellet has been washed once in PBS and resuspended in 1% BSA/2 mM EDTA/PBS. The cell suspension was stratified on a Histopaque solution (Sigma-Aldrich) whose density was adjusted to 1,065 g/ml by addition of PBS and the gradient thus formed has been centrifuged at 800 g for 20 minutes at room temperature. The upper phase, containing a small amount of lymphocytes and abundant tumor cells has been collected at the interphase (about 35 ml) and after a wash in 1% BSA/2 nM EDTA/PBS, cells have been resuspended in spheroid culture medium (see below). The gradient pellet, composed by erythrocytes, lymphocytes and a smaller number of tumor cells, has been resuspended and incubated with ACK buffer in order to lyse erythrocytes for 15 min at room temperature. After the lysis, cells were centrifuged again and washed with PBS. Afterwards, cells were plated in culture medium for adherence (see below)—

Adherent culture conditions: RPMI medium/GlutaMax with 10% FBS and 1 mM Pen/Strep. In these conditions, primary tumor cells form a monolayer on plastic culture plates.

Spheroid culture conditions: cells have been resuspended at a density of 100,000/ml in Dulbecco's modified Eagle's medium/F12 (Invitrogen) supplemented with 1% BSA, 0.5% Glucose, 20 µg/ml insulin (Sigma-Aldrich), 15 mM Hepes, B27 without retinoic acid (Invitrogen), 4 µg/ml heparin (Sigma-Aldrich), 20 ng/ml epidermal growth factor (EGF) and 20 ng/ml basic fibroblast growth factor (bFGF) and plated in non-treated plates for cell culture (Falcon) or in Ultra-Low binding plates (Corning). Under these conditions, cancer cells with stem cell features can form three-dimensional structures called spheroids. Growth factors (EGF and BFGF) have been added every 2-3 days and culture medium replaced every 7 days. After their formation, spheres were disaggregated mechanically or via incubation in Accumax (Innovative Cell Technologies Inc.). The cell suspension has been plated again in the same conditions described above in order to show spheroid propagation (sphere formation assay).

Protein extracts have been prepared from cells derived from MPEs and cultured in adherence or as spheroids, and have been analyzed by Western Blotting. In detail, 25 µg of extracts have been loaded onto NuPage gels 4-12% (Invitrogen) and transferred on nitrocellulose membranes. In order to detect HER3 expression, the anti-HER3 antibody from Santa Cruz has been utilized. Furthermore, also EGFR and HER2 expression has been measured by Western Blotting with anti-EGFR (Santa Cruz) and anti-HER2 antibodies (RnD systems) respectively. As negative control, extracts from the cervical cancer cell line HeLa have been utilized. HER3 expression is approximately 5-fold higher when cells are grown as spheroids as compared to adherent cells (FIG. 4A). Likewise, also the expression of HER3 ligand, heregulin α, β (HRG-α, β measured with anti-HRG, NeoMarkers) increases in spheroids. In contrast, EGFR and HER2 expression is completely shut off in spheroid cultures. These data suggest that HER3 and the PI3K/AKT signalling axis may have an important role for the cancer stem cell propagation in lung cancer.

Example 5

Inhibition of Signalling, Proliferation and Spheroid Formation of Primary Lung Cancer Cells In order to assess the effect of anti-HER3 antibodies on MPE-derived cells, primary cultures have been plated in spheroid medium in the absence of FBS and treated with antibodies A3 or A4 at the concentration of 10 µg/ml for 1 hour before the preparation of protein extracts. The effect on HER3 phosphorylation has been monitored by Western Blotting using an anti-pHER3 antibody (Cell Signaling). As shown in FIG. 4B, antibodies A3 and A4 were able to reduce 23 and 67%, respectively, the level of HER3 phosphorylation. An antibody of the same isotype used as negative control did not show any effect.

In order to verify the effect of anti HER3 antibodies on the ability of cells to grow in adherent conditions, cells derived from MPEs have been cultured with A3 or A4 at the concentration of 10 µg/ml, 2 wells for each experimental point. After 10 days cells were detached, stained with Trypan Blue (Sigma), and the number of living cells determined at a Zeiss Axjovert 25 microscope (Jena, Germany). Results are shown in FIG. 5A and indicate that tumor cell proliferation is inhibited with Antibodies A3 and A4, 22 and 36% respectively.

Lastly, the inhibitory activity of A3 and A4 on spheroid formation, has been assessed in a spheroid forming assay. After trypsin treatment, MPE-derived cells from adherent cultures have been seeded in 24-well plates in spheroid forming condition in the presence of A3, A4 or isotype negative control, at the concentration of 10 µg/ml, 3 wells for each experimental condition, and kept in culture for 10 days. At the end of this incubation time, sphere number has been determined with a Zeiss Axj overt 25 microscope (Jena, Germany). The total number of spheres/well was determined and the average number for the 3 wells was calculated. Sphere counts has been determined by two independent operators with comparable results. FIG. 5B shows that both A3 and A4 are able to significantly reduce the number of spheres by 22% and 46% respectively.

Example 6

Antitumor Efficacy on Pancreatic Tumors in Nude Mice

In order to assess the therapeutic potential of anti-HER3 antibodies, A3 and A4 have been tested in CD1 nude mice bearing palpable tumors derived from the implantation of cells from the human tumor cell line BxPC3. In detail, $1 \times 10^7$ BxPC3 cells have been injected subcutaneously (s.c.) in the right flank of each mouse in the presence of matrigel (Reduced growth factor matrigel, BD bioscience). After 7 days, when tumors had reached the size of 200 mm$^3$, mice were randomized in homogeneous groups and treated with 3 weekly injections of A3, A4 or control antibody of the same isotype at the dose of 25 mg/kg i.p. Results are presented in FIG. 6A and show that both A3 and A4 are able to block pancreatic tumor progression.

Example 7

Antitumor Efficacy on Spontaneous Mammary Tumors in Transgenic Mice.

In a vast majority of cases the efficacy of therapeutic compounds against cancer is studied in immuno-deficient mice implanted with s.c tumors, as described in the previous example. However these models, while allowing to show efficacy on tumor cells of human origin, present the limitation of not being able to evaluate the therapeutic effect on spontaneous tumorigenesis, and to appreciate the influence of the immune system on the system of interest.

For this reasons, the BALB/neuT mouse model has been utilized. These animals express the oncogenic form of the rat HER-2/neu receptor, specifically in the mammary gland. This tissue specific expression induces the appearance of hyperplasia at the 10$^{th}$ week of life and of adenocarcinomas between the 15$^{th}$ and the 20$^{th}$ week of life [25]. Evidences in literature suggest that in HER-2/neu transgenic mice, HER-3 is expressed and has an active role in the development and aggressiveness of mammary tumors [26]. Furthermore, vaccination studies performed with whole cell vaccines expressing ErbB family receptor members, including also HER3, have shown some antitumor efficacy in this murine model [27].

In order to assess the therapeutic efficacy of anti-HER3 antibodies in the BALB/neuT model, 2 groups of 4 mice have been utilized in which the size of a reference developing tumor was about 40 mm$^3$ as measured by ultrasound with the instrument VEVO 770 (Visualsonics), and bearing less than 2 tumors/mouse. The first group has been treated with a negative control antibody of the same isotype, while the second has been treated with the antibody A3. Antibody A4 has not been utilized because it does not cross-react with mouse HER-3. Antibodies were injected twice/week i.p. at the dose of 25 mg/kg. Every 7 days the size of reference tumors was measured by ultrasound imaging and the tumor multiplicity by palpation. FIG. 6B shows that antibody A3, compared with the negative control, is able to slow down the growth of the reference tumors. Furthermore, FIG. 7A shows a significant effect on tumor multiplicity over time ($p<0.01$). As a final confirmation of these results, at the end of the study (week 4), mice have been euthanized, tumors explanted and weight determined.

The table below shows the difference between the experimental groups.

|         | A3    | Contr. IgG |
|---------|-------|------------|
| #1      | 0.869 | 5.934      |
| #2      | 0.695 | 3.151      |
| #3      | 3.282 | 7.500      |
| #4      | 1.121 | 6.389      |
| Media   | 1.492 | 5.744      |
| St- Dev | 1.2   | 1.8        |

Example 8

Synergic Efficacy of A3 and A4 Monoclonal Antibodies with HERCEPTIN™ (Trastuzumab)

In literature there are evidences that the combination of monoclonal antibodies against EGFR and HER2 can lead to increased anti-tumor efficacy as a consequence of the simultaneous inhibition of heterodimeric receptor complexes that contribute to cell transformation [28]. In order to assess whether A3 and A4 antibodies could have a synergistic effect with the anti-HER2 monoclonal antibody HERCEPTIN™ (trastuzumab), a combination study has been performed on MCF-7 cells. 2000 cells/well have been seeded in 96 well plates in culture medium with 10% FBS over night. Cells have then been washed with PBS and incubated in quadruplicates with the antibodies at the concentration of 10 mg/ml, as single agent or in combination with HERCEPTIN™ (trastuzumab) at the same concentration, in medium with 1% FBS and incubated for 6 days. The MTT dye (Sigma) has been added and incubated for 60 minutes. Absorbance has then been measured with an ELISA reader at 570 nm. The results in FIG. 7B show that MCF-7 proliferation at low serum concentrations and in the presence of NRG is not affected by HERCEPTIN™ (trastuzumab). In contrast, both A3 and A4 inhibit cell proliferation approximately 30% and 40%, respectively. Inhibition increased above 50% when HERCEPTIN™ (trastuzumab) is added to A3 or to A4.

Example 9

Sequence of CDRs

In order to generate an antibody suitable for therapeutic application in humans, the amino acid sequence of antibodies A3 and A4 has been determined by sequencing the cDNA obtained from the relevant hybridomas. Total RNA has been extracted from $10^7$ pelleted A3 and A4 hybridoma cells, utilizing the Qiagen RNeasy mini kit (Cat No: 74104). The purified RNA has been resuspended in 50 µl of water and its quality checked by electrophoresis on a 1.2% agarose gel. cDNAs for $V_H$ and $V_L$ regions have been generated with primers specific for IgGs and constant regions. cDNAs have been then amplified by PCR utilizing oligonucleotides that paired in the signal peptide sequence. Amplified DNA has been purified from gel and cloned in the vector pGEM-T-Easy (Promega). DNA extracted from clones $V_H$ and $V_L$ thus obtained has been sequenced on both strands. The localization of the complementarity determining regions (CDRs) within the sequence has been determined by alignment with sequences of other antibodies [29]

Antibody A3

The DNA sequence of regions VL and VH is indicated in SEQ ID: 5 and 6. The corresponding amino acid sequences are shown in SEQ ID: 7 and 8. Five independent clones provided identical sequences.

Antibody A4

The DNA sequence of regions VL and VH is indicated in SEQ ID: 9 and 10. The corresponding amino acid sequences are shown in SEQ ID: 11 and 12. Six independent clones provided identical sequences with the exception of a single amino acid substitution in one clone.

Example 10

Antibody A3 Epitope Mapping.

To identify the epitope recognized by A3 antibody, a human ErbB3 peptide collection consisting of 158 15mer peptides overlapping by 11 residues (Jerini Peptide Technologies, Berlin, Germany) has been utilized. Each peptide was resuspended in DMSO at 40 mg/ml and diluted in sodium carbonate buffer (10 mM, pH 9.6) at 1 µg/ml in 96well plates (Nunc Maxisorp) at a volume of 100 µl/well and incubated over night at 4° C. Human ErbB3 ECD-Fc protein (RnD) and buffer coated wells were used as positive and negative controls of the assay, respectively. The day after, plates were washed with 200 µl PBS 1× pH 7.4 and blocked with PBS 5% BSA for 2 hr at room temperature. After three washes with PBS, 0.05% Tween20 (PBST), plates were incubated for 2 hours at room temperature with A3 antibody diluted at 1 µg/ml in PBST, 1% BSA for 2 hours at room temperature. Plates were then washed three times in PBST and then incubated with 1/5000 diluted goat anti-mouse IgG HRP conjugated (Abcam) for one hour. After three washing in PBST, 100 µl/well 3, 3', 5, 5'-Tetramethylbenzidine (TMB) Liquid Substrate (Sigma) were added and the reaction stopped 20 minutes later with 50 µl/well Stop Reagent for TMB Substrate (Sigma). $OD_{450}$ was determined at an ELISA reader (Perkin Elmer).

The results of the assay are shown in FIG. 8A and clearly show that a main single epitope is recognized by A3. The peptide sequence of the epitope is as follows: QCNGHCF-GPNPNQCC (SEQ ID: 68). Analysis of ErbB3 crystal structure [30] by CnD4.3 software mapped the epitope mostly in ErbB3 finger loop of domain II (see FIG. 8B). These data suggest that A3 antibody, in addition to the above described properties, has the potential to act as inhibitor of ErbB3 dimerization.

Example 11

Antibody A4 Humanization.

In order to generate a humanized antibody, the method of super-humanization described in Hwang et al [31] has been chosen. According to the method, antibody A4 has been classified in this manner: light chain kappa, with combination of Canonical Structures (CS) 6-1-1: heavy chain with combination of CS 1-2-x. Assignment of the J segment is JK2 for the light chain kappa, JH4 for the heavy chain. Since residue 71 is a valine, for the CDR-H2 a CS2 has been assigned. The human germline VH1-2*02 has been chosen for the heavy chain because there are evidences that VH1-2*02 should have a combination of CS 1-2-x. Furthermore, CDRs of the sequence VH1-2*02 (CDR-H1 and CDR-H2)

are those most similar to the CDR sequences of the murine antibody. For the light chain the choice has been the human germline IGKV3-20*01 (CSs 6-1-1).

From the comparison of the murine A4 CDRs and the selected human germline CDRs, the sequences indicated in SEQ ID: 13 and 14 (Light and Heavy chain respectively) have been designed, and synthetic genes generated by assembly of synthetic oligonucleotides followed by PCR according to the method described in Stemmer et al [32]. The sequences generated are indicated in SEQ ID: 15 and 16. Synthetic genes have then been cloned by recombination, using the Gateway system (Invitrogen) in plasmids pBS-EF1α-HCl and pBS-EF1α-LCK carrying the synthetic gens coding for the human IgG type 1 Heavy Chain and kappa Light chain respectively. The vectors thus obtained have been called pHC1-humA4 and pLCK-hum A4, respectively.

Example 12

Expression and Specificity of Hum-A4 Antibody.

A total of 5 μg of plasmids PHC1-humA4 and PLCK-humA4 has been transfected with Lipofectamine 2000 (Invitrogen) in 293-EBNA cells (Invitrogen), seeded in 6 cm plates at a molar ratio of 7:3. As controls the cDNAs from a control immunoglobulin against a different antigen and that of the original murine A4 antibody have been cloned in pBS-EF1α.

After transfection, cells have been incubated for one week before collecting the supernatant. Immunoglobulins have been quantified with a ForteBio biosensor (CA, US) and analyzed by Coomassie staining in native and denaturing conditions (FIG. 9A). All immunoglobulins were produced in similar amounts.

In order to assess the ability of IgGs to bind protein HER3, an ELISA assay has been performed utilizing amounts from 5 to 0.04 mg of IgGs/well. Results in FIG. 9B show that humA4 is able to bind human HER3 with an efficiency similar to the murine antibody.

REFERENCES

1) Hsieh A C and Moasser M M. *Br. J. Cancer.* 2007; 97: 453
2) Kruser T J et al. *Exp Cell Res.* 2010; 316:1083
3) Mittendorf E A et al. *Cancer* 2006; 106:2309
4) Peoples G E et al. *J Clin Oncol* 2005; 23:7536
5) Mittendorf E A, et al. *Ann Surg Oncol* 2006; 13:1085
6) Aurisicchio L et al. *Clin Cancer Res.* 2009; 15:1575
7) Fattori E et al. *Hum Gene Ther.* 2009; 20:253
8) Peruzzi D et al. *Vaccine.* 2010; 28:1201
9) Moasser M M *Oncogene* 2007; 26: 6577
10) Berger M B et al. *Febs Lett* 2004; 569: 332
11) Prigent S A et al. *EMBO J* 1994; 13: 2831
12) Engelman J A et al. *Science* 2007; 316: 1039
13) Zhou J et al. *Proc Natl Acad Sci USA* 2007; 104: 16158
14) Dubrovska et al. *Proc Natl Acad Sci USA* 2009; 106: 268
15) Yang Y et al *PLOS one,* 2008; 3: e2220
16) Vermuelen L et al. *Proc Natl Acad Sci USA* 2008; 105: 13427
17) Hambardzumyan D et al. *Genes & Dev* 2008; 22: 436
18) Yilmaz O H et al. *Nature* 2006; 441: 475
19) Schoeberl et al. *Science Signaling* 2009; 2: ra31
20) Schoeberl et al. *Cancer Res* 2010; 70:2485
21) Fattori E et al. *Somat Cell Mol Genet.* 2002; 27:75
22) Kani et al., *J Biol Chem* 2005; 280: 8238
23) Sheng Q et al. *Cancer Cell.* 2010; 17:298
24) Basak S K et al. *PLoS One.* 2009; 4:e5884
25) Lucchini F et al. *Cancer Lett* 1992; 64:203
26) Kim at al. *Breast Cancer Research* 2005, 7:R708
27) Masuelli L et al. *Int J Oncol.* 2007; 30:381
28) Ye, D. et al. 1999. *Oncogene* 18:731-738
29) Kabat E A et al. *J Immunol.* 1991; 147:1709
30) Cho H S et al., *Science.* 2002; 297: 1330-1333
31) Hwang W Y et al. *Methods* 2005, 36:35
32) Stemmer W P et al. *Gene* 164:49-53
33) Pearson W. R. *Methods Mol. Biol.* 1994, 24: 307-331
34) Gonnet et al. *Science* 1992, 256: 1443-45
35) Maston G. A. *Annu. Rev. Genomics Hum. Genet.* 2006, 7:29-59
36) Koprowski et al. *Curr Top Microbiol Immunol.* 1998, 226:V-XIII
37) Qiu X.-Q. et al. *Nature biotechnology* 2007, 25(8):921-929
38) Almagro J. C et al. *Frontiers in Bioscience* 2008, 13:1619-33
39) Dall'Acqua W. F.et al. *Methods* 2005, 36:43-60
40) Damschroder M. M. et al. *Molecular Immunology* 2007, 44:3049-3060
41) Qin W. et al. *Molecular Immunology* 2007, 44:2355-2361
42) Chang H. et al. *Molecular Immunology* 2007, 44:3789-3796
43) Pearson W. R. *Methods Mol Biol.* 2000, 132:185-219
44) Altschul S. F. et al. *J. Mol. Biol.* 1990, 215:403-410
45) Scarano S. et al. *Biosens Bioelectron.* 2010, 25(5):957-66

The invention claimed is:

1. An ErbB3 antibody comprising:
   a) (i) a light chain CDR1 sequence as set forth in SEQ ID NO: 17,
   (ii) a light chain CDR2 sequence as set forth in SEQ ID NO: 18,
   (iii) a light chain CDR3 sequence as set forth in SEQ ID NO: 19,
   (iv) a heavy chain CDR1 sequence as set forth in SEQ ID NO: 20,
   (v) a heavy chain CDR2 sequence as set forth in SEQ ID NO: 21, and
   (vi) a heavy chain CDR3 sequence as set forth in SEQ ID NO: 22; or
   b) (i) a light chain CDR1 sequence as set forth in SEQ ID NO: 29,
   (ii) a light chain CDR2 sequence as set forth in SEQ ID NO: 30,
   (iii) a light chain CDR3 sequence as set forth in SEQ ID NO: 25,
   (iv) a heavy chain CDR1 sequence as set forth in SEQ ID NO: 31,
   (v) a heavy chain CDR2 sequence as set forth in SEQ ID NO: 32, and
   (vi) a heavy chain CDR3 sequence as set forth in SEQ ID NO: 28.

2. A pharmaceutical composition, which comprises the antibody or an antigen-binding fragment thereof of claim 1 and a pharmaceutically acceptable carrier or excipient.

* * * * *

SEQUENCE LISTING

```
<160> NUMBER OF SEQ ID NOS: 68

<210> SEQ ID NO 1
<211> LENGTH: 4032
<212> TYPE: DNA
<213> ORGANISM: Artificial Sequence
<220> FEATURE:
<223> OTHER INFORMATION: Codon optimized coding sequence encoding full
      length human HER3, wherein the encoded HER3 has a His to Phe
      mutation at position 584

<400> SEQUENCE: 1
atgagggcca acgacgccct gcaggtgctg ggcctgctgt tcagcctcgc tagggggcagc        60 gaggtcggca acagccaggc cgtgtgccca ggcacactga acggcctgag cgtgactggc       120
```

```
gacgctgaga accagtacca gaccctgtac aagctgtacg agagatgcga ggtggtgatg      180
ggcaacctgg aaatcgtgct gaccggccac aacgccgacc tgagcttcct gcagtggatc      240
agagaggtga ccggctacgt cctggtcgcc atgaacgagt tcagcaccct gccactgccc      300
aatctcaggg tcgtgcgcgg cacccaggtg tacgacggca agttcgccat cttcgtgatg      360
ctgaactaca acaccaacag cagccacgcc ctgaggcagc tgaggctgac ccagctgacc      420
gagatcctgt ctggcggcgt gtacatcgag aagaacgaca agctgtgcca catggacacc      480
atcgactggc gggacatcgt gagggacagg gacgccgaga tcgtggtgaa ggacaacggc      540
agaagctgcc cccctgcca cgaggtctgc aagggcagat gctggggccc tggcagcgag      600
gactgccaga ccctgaccaa gaccatctgc gcccctcagt gcaacggcca ctgcttcggc      660
cccaacccca accagtgctg ccacgacgag tgcgctggcg gctgtagcgg acctcaggac      720
accgactgct tcgcctgcag acacttcaac gacagcggcg cctgcgtgcc caggtgcccc      780
cagcccctgg tgtacaacaa gctgaccttc agctggaaac ccaaccccca caccaagtac      840
cagtacggcg gcgtgtgcgt ggccagctgc cctcacaact tcgtggtgga ccagaccagc      900
tgcgtgagag cctgccccc tgacaagatg gaagtggaca agaacggact gaagatgtgc      960
gagccctgtg gcggcctgtg ccccaaggcc tgcgagggca ccggcagcgg cagcaggttc     1020
cagaccgtgg acagcagcaa catcgacggc ttcgtgaact gcaccaagat cctgggcaat     1080
ctggacttcc tgatcaccgg cctgaacggc gaccctggc acaagatccc cgccctggac     1140
cccgagaagc tgaacgtgtt caggaccgtg agagagatca ccggctacct gaacatccag     1200
agctggcccc ctcacatgca aacttcagc gtgttcagca acctgaccac catcggcggc     1260
agaagcctgt acaacagggg cttcagcctg ctgatcatga agaacctgaa cgtgaccagc     1320
ctgggcttca aagcctgaa agagatcagc gccggcagga tctacatcag cgccaacagg     1380
cagctgtgct accaccacag cctgaactgg accaaggtgc tgaggggccc caccgaggaa     1440
aggctggaca tcaagcacaa caggcccagg cgggactgtg tggctgaggg caaagtctgc     1500
gaccccctgt gcagcagcgg cggctgttgg ggaccaggcc caggccagtg tctgagctgc     1560
aggaactaca gcaggggcgg agtctgtgtc acccactgca acttctctgaa tggcgagccc     1620 agagagttcg cccacgaggc cgagtgcttc agctgccacc ccgagtgcca gcccatggaa     1680
ggcaccgcca cctgcaacgg cagcggctcc gacacctgcg cccagtgcgc ccacttcagg     1740
gacggccctt tctgcgtgag cagctgtccc cacggcgtgc tgggcgcaaa gggacccatc     1800
tacaagtacc ccgacgtgca gaacgagtgc aggccttgcc acgagaactg cacccagggc     1860
tgcaaaggcc cagagctgca ggactgtctg ggccagacac tggtgctgat cggcaagacc     1920
cacctgacca tggcccctgac cgtgatcgcc ggcctggtgg tgatctttat gatgctgggc     1980
ggcaccttcc tgtactggcg gggcagaagg attcagaaca gagggccat gagaagatac     2040 ctggaaaggg gcgagagcat cgagcccctg gaccctagcg agaaggccaa caaggtgctg     2100
gccaggatct tcaaagagac agagctgagg aagctgaagg tgctgggaag cggcgtgttc     2160
ggcaccgtgc acaagggcgt gtggattccc gagggcgagt ccatcaagat ccctgtgtgc     2220
atcaaggtga tcgaggacaa gagcggcagg cagtccttcc aggccgtgac cgaccacatg     2280
ctggccatcg gcagcctgga ccacgcccac atcgtgagac tgctgggact gtgccctggc     2340
tccagcctgc agctggtgac ccagtacctg cccctgggca gcctgctgga ccacgtgagg     2400
cagcacagag gcgccctggg cccccagctg ctgctgaatt ggggagtgca gatcgccaag     2460
ggcatgtact acctggaaga gcacggcatg gtgcacagga acctggcagc aaggaacgtg     2520
```

```
ctgctgaaga gccccagcca ggtgcaggtg gccgacttcg gagtggcaga tctcctgcca    2580
cccgacgaca agcagctgct gtacagcgag gccaagaccc ccatcaagtg gatggccctg    2640
gaaagcatcc acttcggcaa gtacacccac cagagcgacg tgtggagcta cggcgtgacc    2700
gtgtgggagc tgatgacctt cggcgccgag ccctacgccg gcctgaggct ggccgaggtg    2760
ccagacctgc tggaaaaggg cgagcggctg gctcagccac agatctgcac catcgacgtg    2820
tacatggtga tggtgaagtg ctggatgatc gacgagaaca tcaggcccac cttcaaagag    2880
ctggccaacg agttcaccag gatggccagg gaccccccta gatacctggt gatcaagaga    2940
gagagcggcc tggaatcgc ccctggcccc gagcctcacg gcctgaccaa caagaagctg    3000
gaagaggtcg agctggaacc agagctggac ctggatctgg acctggaagc cgaggaagat    3060
aacctggcca ccaccaccct gggctccgct ctgtctctgc ctgtcggcac actgaacaga    3120
cccagaggat ctcagagcct cctgtcccc agcagcggct acatgcccat gaaccaggga    3180
aacctgggcg agagctgtca ggaaagcgcc gtcagcggca gctccgagag gtgccccagg    3240
cccgtgagcc tgcaccccat gcccaggggc tgcctggcca gcgagtccag cgagggccac    3300
gtgaccggca gcgaggccga actccaggaa aaggtgtcaa tgtgcagaag caggtccaga    3360
agcagaagcc ccagacccag gggcgacagc gcctaccaca gcagaggca ctccctgctg    3420
accccgtga ccccctgag ccctcccggc ctggaagagg aagatgtgaa cggatacgtg    3480
atgcccgaca cccacctgaa gggcacccct agcagcagag agggcaccct gagcagcgtg    3540
ggcctgtcct ccgtgctggg caccgaggaa gaggatgagg acgaggaata cgagtacatg    3600
aacaggcgga gaaggcacag ccccccctcac ccccccagac ctagctctct ggaagagctg    3660
ggctatgagt acatggacgt gggcagcgac ctgagcgcct ctctgggcag cacacagagc    3720
tgccctctgc accccgtgcc tatcatgccc accgccggca ccaccccga tgaggattac    3780
gaatatatga atagacagag ggatggcggc ggaccaggcg gcgactatgc cgcaatgggc    3840
gcctgtcccg ccagcgagca gggatacgag gaaatgaggg ccttccaggg cccaggccac    3900
caggcccccc acgtgcacta cgccaggctg aaaaccctga gaagcctgga agccaccgac    3960
tccgccttcg acaaccccga ctactggcac agcaggctgt ccctaaggc caacgcccag    4020
aggacctgat ga                                                       4032
```

<210> SEQ ID NO 2
<211> LENGTH: 1309
<212> TYPE: PRT
<213> ORGANISM: Artificial Sequence
<220> FEATURE:
<223> OTHER INFORMATION: human HER3 with a His to Phe mutation at
      position 584

<400> SEQUENCE: 2

```
Met Arg Ala Asn Asp Ala Leu Gln Val Leu Gly Leu Leu Phe Ser Leu
1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80
```

-continued

```
Arg Glu Val Thr Gly Tyr Val Leu Val Ala Met Asn Glu Phe Ser Thr
             85                  90                  95
Leu Pro Leu Pro Asn Leu Arg Val Val Arg Gly Thr Gln Val Tyr Asp
        100                 105                 110
Gly Lys Phe Ala Ile Phe Val Met Leu Asn Tyr Asn Thr Asn Ser Ser
            115                 120                 125
His Ala Leu Arg Gln Leu Arg Leu Thr Gln Leu Thr Glu Ile Leu Ser
    130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                165                 170                 175
Lys Asp Asn Gly Arg Ser Cys Pro Pro Cys His Glu Val Cys Lys Gly
            180                 185                 190
Arg Cys Trp Gly Pro Gly Ser Glu Asp Cys Gln Thr Leu Thr Lys Thr
        195                 200                 205
Ile Cys Ala Pro Gln Cys Asn Gly His Cys Phe Gly Pro Asn Pro Asn
    210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
        275                 280                 285
Ser Cys Pro His Asn Phe Val Val Asp Gln Thr Ser Cys Val Arg Ala
    290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
        355                 360                 365
Asn Gly Asp Pro Trp His Lys Ile Pro Ala Leu Asp Pro Glu Lys Leu
    370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
            420                 425                 430
Met Lys Asn Leu Asn Val Thr Ser Leu Gly Phe Arg Ser Leu Lys Glu
        435                 440                 445
Ile Ser Ala Gly Arg Ile Tyr Ile Ser Ala Asn Arg Gln Leu Cys Tyr
    450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
```

-continued

```
              500                 505                 510
Gly Pro Gly Gln Cys Leu Ser Cys Arg Asn Tyr Ser Arg Gly Gly Val
          515                 520                 525
Cys Val Thr His Cys Asn Phe Leu Asn Gly Glu Pro Arg Glu Phe Ala
          530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                  565                 570                 575
Ala His Phe Arg Asp Gly Pro Phe Cys Val Ser Ser Cys Pro His Gly
              580                 585                 590
Val Leu Gly Ala Lys Gly Pro Ile Tyr Lys Tyr Pro Asp Val Gln Asn
              595                 600                 605
Glu Cys Arg Pro Cys His Glu Asn Cys Thr Gln Gly Cys Lys Gly Pro
          610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                  645                 650                 655
Met Met Leu Gly Gly Thr Phe Leu Tyr Trp Arg Gly Arg Arg Ile Gln
              660                 665                 670
Asn Lys Arg Ala Met Arg Arg Tyr Leu Glu Arg Gly Glu Ser Ile Glu
              675                 680                 685
Pro Leu Asp Pro Ser Glu Lys Ala Asn Lys Val Leu Ala Arg Ile Phe
          690                 695                 700
Lys Glu Thr Glu Leu Arg Lys Leu Lys Val Leu Gly Ser Gly Val Phe
705                 710                 715                 720
Gly Thr Val His Lys Gly Val Trp Ile Pro Glu Gly Glu Ser Ile Lys
                  725                 730                 735
Ile Pro Val Cys Ile Lys Val Ile Glu Asp Lys Ser Gly Arg Gln Ser
              740                 745                 750
Phe Gln Ala Val Thr Asp His Met Leu Ala Ile Gly Ser Leu Asp His
          755                 760                 765
Ala His Ile Val Arg Leu Leu Gly Leu Cys Pro Gly Ser Ser Leu Gln
          770                 775                 780
Leu Val Thr Gln Tyr Leu Pro Leu Gly Ser Leu Leu Asp His Val Arg
785                 790                 795                 800
Gln His Arg Gly Ala Leu Gly Pro Gln Leu Leu Leu Asn Trp Gly Val
                  805                 810                 815
Gln Ile Ala Lys Gly Met Tyr Tyr Leu Glu Glu His Gly Met Val His
              820                 825                 830
Arg Asn Leu Ala Ala Arg Asn Val Leu Leu Lys Ser Pro Ser Gln Val
              835                 840                 845
Gln Val Ala Asp Phe Gly Val Ala Asp Leu Leu Pro Pro Asp Asp Lys
          850                 855                 860
Gln Leu Leu Tyr Ser Glu Ala Lys Thr Pro Ile Lys Trp Met Ala Leu
865                 870                 875                 880
Glu Ser Ile His Phe Gly Lys Tyr Thr His Gln Ser Asp Val Trp Ser
                  885                 890                 895
Tyr Gly Val Thr Val Trp Glu Leu Met Thr Phe Gly Ala Glu Pro Tyr
              900                 905                 910
Ala Gly Leu Arg Leu Ala Glu Val Pro Asp Leu Leu Glu Lys Gly Glu
          915                 920                 925
```

```
Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
            965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
            995                 1000                1005

Leu Asp Leu Asp Leu Asp Leu Glu Ala Glu Glu Asp Asn Leu Ala
    1010            1015                1020

Thr Thr Thr Leu Gly Ser Ala Leu Ser Leu Pro Val Gly Thr Leu
    1025            1030                1035

Asn Arg Pro Arg Gly Ser Gln Ser Leu Leu Ser Pro Ser Ser Gly
    1040            1045                1050

Tyr Met Pro Met Asn Gln Gly Asn Leu Gly Glu Ser Cys Gln Glu
    1055            1060                1065

Ser Ala Val Ser Gly Ser Ser Glu Arg Cys Pro Arg Pro Val Ser
    1070            1075                1080

Leu His Pro Met Pro Arg Gly Cys Leu Ala Ser Glu Ser Ser Glu
    1085            1090                1095

Gly His Val Thr Gly Ser Glu Ala Glu Leu Gln Glu Lys Val Ser
    1100            1105                1110

Met Cys Arg Ser Arg Ser Arg Ser Arg Ser Pro Arg Pro Arg Gly
    1115            1120                1125

Asp Ser Ala Tyr His Ser Gln Arg His Ser Leu Leu Thr Pro Val
    1130            1135                1140

Thr Pro Leu Ser Pro Pro Gly Leu Glu Glu Glu Asp Val Asn Gly
    1145            1150                1155

Tyr Val Met Pro Asp Thr His Leu Lys Gly Thr Pro Ser Ser Arg
    1160            1165                1170

Glu Gly Thr Leu Ser Ser Val Gly Leu Ser Ser Val Leu Gly Thr
    1175            1180                1185

Glu Glu Glu Asp Glu Asp Glu Glu Tyr Glu Tyr Met Asn Arg Arg
    1190            1195                1200

Arg Arg His Ser Pro Pro His Pro Pro Arg Pro Ser Ser Leu Glu
    1205            1210                1215

Glu Leu Gly Tyr Glu Tyr Met Asp Val Gly Ser Asp Leu Ser Ala
    1220            1225                1230

Ser Leu Gly Ser Thr Gln Ser Cys Pro Leu His Pro Val Pro Ile
    1235            1240                1245

Met Pro Thr Ala Gly Thr Thr Pro Asp Glu Asp Tyr Glu Tyr Met
    1250            1255                1260

Asn Arg Gln Arg Asp Gly Gly Gly Pro Gly Gly Asp Tyr Ala Ala
    1265            1270                1275

Met Gly Ala Cys Pro Ala Ser Glu Gln Gly Tyr Glu Glu Met Arg
    1280            1285                1290

Ala Phe Gln Gly Pro Gly His Gln Ala Pro His Val His Tyr Ala
    1295            1300                1305

Arg
```

<210> SEQ ID NO 3
<211> LENGTH: 1929
<212> TYPE: DNA
<213> ORGANISM: Artificial Sequence
<220> FEATURE:
<223> OTHER INFORMATION: Codon optimized coding sequence encoding the
human HER3 extracellular domain, wherein the encoded HER3 domain
has a His to Phe mutation at position 584

<400> SEQUENCE: 3

```
atgagggcca acgacgccct gcaggtgctg ggcctgctgt tcagcctcgc tagggcagc        60
gaggtcggca acagccaggc cgtgtgccca ggcacactga acggcctgag cgtgactggc       120
gacgctgaga accagtacca gaccctgtac aagctgtacg agagatgcga ggtggtgatg       180
ggcaacctgg aaatcgtgct gaccggccac aacgccgacc tgagcttcct gcagtggatc       240
agagaggtga ccggctacgt cctggtcgcc atgaacgagt tcagcaccct gccactgccc       300
aatctcaggg tcgtgcgcgg cacccaggtg tacgacggca agttcgccat cttcgtgatg       360
ctgaactaca caccaacag cagccacgcc ctgaggcagc tgaggctgac ccagctgacc        420
gagatcctgt ctggcggcgt gtacatcgag aagaacgaca gctgtgcca catggacacc        480
atcgactggc gggacatcgt gagggacagg gacgccgaga tcgtggtgaa ggacaacggc       540
agaagctgcc ccccctgcca cgaggtctgc aagggcagat gctggggccc tggcagcgag       600
gactgccaga ccctgaccaa gaccatctgc gcccctcagt gcaacggcca ctgcttcggc       660
cccaaccccca ccagtgctg ccacgacgag tgcgctggcg gctgtagcgg acctcaggac       720
accgactgct cgcctgcag acacttcaac gacagcggcg cctgcgtgcc caggtgcccc       780
cagcccctgg tgtacaacaa gctgaccttc cagctggaac caaccccca caccaagtac       840
cagtacggcg cgtgtgcgt ggccagctgc cctcacaact cgtggtgga ccagaccagc       900
tgcgtgagag cctgccccc tgacaagatg gaagtggaca gaacggact gaagatgtgc       960
gagccctgtg gcggcctgtg cccccaaggcc tgcgagggca ccggcagcgg cagcaggttc      1020
cagaccgtgg acagcagcaa catcgacggc ttcgtgaact gcaccaagat cctgggcaat      1080
ctggacttcc tgatcaccgg cctgaacggc gaccccctgg acaagatccc cgccctggac      1140
cccgagaagc tgaacgtgtt caggaccgtg agagagatca ccggctacct gaacatccag      1200
agctggcccc ctcacatgca caacttcagc gtgttcagca acctgaccac catcggcggc      1260
agaagcctgt acaacagggg cttcagcctg ctgatcatga gaaacctgaa cgtgaccagc      1320
ctgggcttca agcctgaa agagatcagc gccggcagga tctacatcag cgccaacagg      1380
cagctgtgct accaccacag cctgaactgg accaaggtgc tgaggggccc caccgaggaa      1440
aggctggaca tcaagcacaa caggcccagg cgggactgtg tggctgaggg caaagtctgc      1500
gacccccctgt gcagcagcgg cggctgttgg ggaccaggcc caggccagtg tctgagctgc      1560
aggaactaca gcaggggcgg agtctgtgtc acccactgca acttcctgaa tggcgagccc      1620
agagagttcg cccacgaggc cgagtgcttc agctgccacc ccgagtgcca gcccatggaa      1680
ggcaccgcca cctgcaacgg cagcggctcc gacacctgcg cccagtgcgc ccacttcagg      1740
gacggcccctt tctgcgtgag cagctgtccc cacggcgtgc tgggcgcaaa gggacccatc      1800
tacaagtacc ccgacgtgca gaacgagtgc aggccttgcc acgagaactg cacccagggc      1860
tgcaaaggcc cagagctgca ggactgtctg ggccagacac tggtgctgat cggcaagacc      1920
cactgatga                                                              1929
```

<210> SEQ ID NO 4

-continued

<211> LENGTH: 641
<212> TYPE: PRT
<213> ORGANISM: Artificial Sequence
<220> FEATURE:
<223> OTHER INFORMATION: Human HER3 extracellular domain, wherein the
      encoded HER3 domain has a His to Phe mutation at position 584

<400> SEQUENCE: 4

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
```

```
                370              375             380
Asn Val Phe Arg Thr Val Arg Glu Ile Thr Gly Tyr Leu Asn Ile Gln
385                 390             395                 400

Ser Trp Pro Pro His Met His Asn Phe Ser Val Phe Ser Asn Leu Thr
                405             410                 415

Thr Ile Gly Gly Arg Ser Leu Tyr Asn Arg Gly Phe Ser Leu Leu Ile
                420             425                 430

Met Lys Asn Leu Asn Val Thr Ser Leu Gly Phe Arg Ser Leu Lys Glu
                435             440                 445

Ile Ser Ala Gly Arg Ile Tyr Ile Ser Ala Asn Arg Gln Leu Cys Tyr
450                 455             460

His His Ser Leu Asn Trp Thr Lys Val Leu Arg Gly Pro Thr Glu Glu
465                 470             475                 480

Arg Leu Asp Ile Lys His Asn Arg Pro Arg Asp Cys Val Ala Glu
                485             490                 495

Gly Lys Val Cys Asp Pro Leu Cys Ser Ser Gly Gly Cys Trp Gly Pro
                500             505                 510

Gly Pro Gly Gln Cys Leu Ser Cys Arg Asn Tyr Ser Arg Gly Gly Val
                515             520                 525

Cys Val Thr His Cys Asn Phe Leu Asn Gly Glu Pro Arg Glu Phe Ala
530                 535             540

His Glu Ala Glu Cys Phe Ser Cys His Pro Glu Cys Gln Pro Met Glu
545                 550             555                 560

Gly Thr Ala Thr Cys Asn Gly Ser Gly Ser Asp Thr Cys Ala Gln Cys
                565             570                 575

Ala His Phe Arg Asp Gly Pro Phe Cys Val Ser Ser Cys Pro His Gly
                580             585                 590

Val Leu Gly Ala Lys Gly Pro Ile Tyr Lys Tyr Pro Asp Val Gln Asn
                595             600             605

Glu Cys Arg Pro Cys His Glu Asn Cys Thr Gln Gly Cys Lys Gly Pro
                610             615             620

Glu Leu Gln Asp Cys Leu Gly Gln Thr Leu Val Leu Ile Gly Lys Thr
625                 630             635                 640

His

<210> SEQ ID NO 5
<211> LENGTH: 360
<212> TYPE: DNA
<213> ORGANISM: Artificial Sequence
<220> FEATURE:
<223> OTHER INFORMATION: Coding sequence of variable light chain region
      of antibody A3

<400> SEQUENCE: 5
gatgttttga tgacccaaac tccactctcc ctgcctgtca gtcttggaga tcaagcctcc     60
atctcttgca gatctagtca gagcattgta catagttatg aaacacccta tttagaatgg    120
tacctgcaga aaccaggcca gtctccaaag ctcctgatct acagagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcca    300
ttcacgttcg gcacggggac aaaattggaa ataaaacggg ctgatgctgc accaactgta    360

<210> SEQ ID NO 6
<211> LENGTH: 375
<212> TYPE: DNA
```

<213> ORGANISM: Artificial Sequence
<220> FEATURE:
<223> OTHER INFORMATION: Coding sequence of variable heavy chain region of antibody A3

<400> SEQUENCE: 6

```
caggtcactc tgaaagagtc tggccctggg aaattgcagc cctcccagac cctcagtctg    60
acttgttctt tttctgggtt ttcactgagc acttatggta tgggtgtagg ttggattcgt   120
cagcctttag ggaagggtct ggagtggctg ccaacatttt ggtggaatga tgataagtac   180
tataattcag ccctgaagag ccggctcaca atctccaagg ataccctcca caaccaggtt   240
ttcctcaaga tctccagtgt ggacactgca gatgctgcca catactactg tgttcaaata   300
gctaacccct attggtactt cgatgtctgg ggcgcaggga ccacggtcac cgtctcctca   360
gccaaaacga caccc                                                   375
```

<210> SEQ ID NO 7
<211> LENGTH: 120
<212> TYPE: PRT
<213> ORGANISM: Mus musculus
<220> FEATURE:
<221> NAME/KEY: BINDING
<222> LOCATION: (1)..(120)
<223> OTHER INFORMATION: Variable light chain region of antibody A3

<400> SEQUENCE: 7

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Tyr Gly Asn Thr Tyr Leu Glu Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Thr Gly Thr Lys Leu Glu Ile Lys
            100                 105                 110

Arg Ala Asp Ala Ala Pro Thr Val
        115                 120
```

<210> SEQ ID NO 8
<211> LENGTH: 125
<212> TYPE: PRT
<213> ORGANISM: Mus musculus
<220> FEATURE:
<221> NAME/KEY: BINDING
<222> LOCATION: (1)..(125)
<223> OTHER INFORMATION: Variable heavy chain region of antibody A3

<400> SEQUENCE: 8

```
Gln Val Thr Leu Lys Glu Ser Gly Pro Gly Lys Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Leu Gly Lys Gly Leu Glu
        35                  40                  45

Trp Leu Ala Asn Ile Trp Trp Asn Asp Asp Lys Tyr Tyr Asn Ser Ala
```

```
                    50                  55                  60
Leu Lys Ser Arg Leu Thr Ile Ser Lys Asp Thr Ser Asn Asn Gln Val
 65                  70                  75                  80

Phe Leu Lys Ile Ser Ser Val Asp Thr Ala Asp Ala Ala Thr Tyr Tyr
                 85                  90                  95

Cys Val Gln Ile Ala Asn Pro Tyr Trp Tyr Phe Asp Val Trp Gly Ala
            100                 105                 110

Gly Thr Thr Val Thr Val Ser Ser Ala Lys Thr Thr Pro
        115                 120                 125

<210> SEQ ID NO 9
<211> LENGTH: 348
<212> TYPE: DNA
<213> ORGANISM: Artificial Sequence
<220> FEATURE:
<223> OTHER INFORMATION: Coding sequence of variable light chain region
      of antibody A4

<400> SEQUENCE: 9
cagattgttc tcacccagtc tccagcaatc atgtctgcat ctccagggga agggtcacc      60 atgacctgca gggccaggtc aagtgtaagt tccagttact tgcactggta ccagcagaag    120
ccaggatctt cccccaaact ctggatttat agcacatcca atctggcttt aggagtccca    180
gctcgcttca gtggcagtgg gtctgggacc tcttactctc tcacaatcag tagtgtggag    240
gctgaggatg ctgccactta ttactgccag cagtatgata gttcccccatt cacgttcggc   300 acggggacaa aattggaaat aaaacgggct gatgctgcac caactgta                 348

<210> SEQ ID NO 10
<211> LENGTH: 363
<212> TYPE: DNA
<213> ORGANISM: Artificial Sequence
<220> FEATURE:
<223> OTHER INFORMATION: Coding sequence of variable heavy chain region
      of antibody A4

<400> SEQUENCE: 10
caggtccaac tgcagcaacc tgggtctgag ctggtgaggc ctggagcttc agtgaagctg      60
tcctgcaagg cttctggcta cacattcacc atcttctgga tccactgggt gaagcagagg    120
cctggacaag gccttgagtg gattggaaat atttatcctg gtagtggtgg aactaactac    180
gatgagaaat tcaagagcaa ggccacactg actgtagaca ttttccag cacagcctac      240 atgcagctca gtagcctgac atctgaggac tctgcggtct attactgtac aagatggggg    300
actgggaagg actactgggg ccaaggcacc actctcaaag tctcctcagc caaaacgaca    360
ccc                                                                  363

<210> SEQ ID NO 11
<211> LENGTH: 116
<212> TYPE: PRT
<213> ORGANISM: Mus musculus
<220> FEATURE:
<221> NAME/KEY: BINDING
<222> LOCATION: (1)..(116)
<223> OTHER INFORMATION: Variable light chain region of antibody A4

<400> SEQUENCE: 11

Gln Ile Val Leu Thr Gln Ser Pro Ala Ile Met Ser Ala Ser Pro Gly
  1               5                  10                  15

Glu Lys Val Thr Met Thr Cys Arg Ala Arg Ser Ser Val Ser Ser Ser
                 20                  25                  30
```

```
Tyr Leu His Trp Tyr Gln Gln Lys Pro Gly Ser Ser Pro Lys Leu Trp
        35                  40                  45

Ile Tyr Ser Thr Ser Asn Leu Ala Leu Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Asp Ser Ser Pro
                85                  90                  95

Phe Thr Phe Gly Thr Gly Thr Lys Leu Glu Ile Lys Arg Ala Asp Ala
                100                 105                 110

Ala Pro Thr Val
        115

<210> SEQ ID NO 12
<211> LENGTH: 121
<212> TYPE: PRT
<213> ORGANISM: Mus musculus
<220> FEATURE:
<221> NAME/KEY: BINDING
<222> LOCATION: (1)..(121)
<223> OTHER INFORMATION: Variable heavy chain region of antibody A4

<400> SEQUENCE: 12

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Ile Phe
                20                  25                  30

Trp Ile His Trp Val Lys Gln Arg Pro Gly Gln Gly Leu Glu Trp Ile
        35                  40                  45

Gly Asn Ile Tyr Pro Gly Ser Gly Gly Thr Asn Tyr Asp Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Trp Gly Thr Gly Lys Asp Tyr Trp Gly Gln Gly Thr Thr Leu
                100                 105                 110

Lys Val Ser Ser Ala Lys Thr Thr Pro
        115                 120

<210> SEQ ID NO 13
<211> LENGTH: 109
<212> TYPE: PRT
<213> ORGANISM: Artificial Sequence
<220> FEATURE:
<223> OTHER INFORMATION: Humanized light chain CDR region of A4 antibody

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
                20                  25                  30

Tyr Leu His Trp Tyr Gln Gln Lys Pro Gly Gln Ala Pro Arg Leu Leu
        35                  40                  45

Ile Tyr Ser Thr Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Asp Ser Ser Pro
                85                  90                  95

Phe Thr Phe Gly Gln Gly Thr Lys Leu Glu Ile Lys Arg
            100                 105
```

<210> SEQ ID NO 14
<211> LENGTH: 116
<212> TYPE: PRT
<213> ORGANISM: Artificial Sequence
<220> FEATURE:
<223> OTHER INFORMATION: Humanized heavy chain CDR region of A4 antibody

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Phe
            20                  25                  30

Trp Met His Trp Val Arg Gln Ala Pro Gly Gln Gly Leu Glu Trp Met
        35                  40                  45

Gly Asn Ile Tyr Pro Gly Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Thr Arg Trp Gly Thr Gly Lys Asp Tyr Trp Gly Gln Gly Thr Leu Val
            100                 105                 110

Thr Val Ser Ser
        115
```

<210> SEQ ID NO 15
<211> LENGTH: 327
<212> TYPE: DNA
<213> ORGANISM: Artificial Sequence
<220> FEATURE:
<223> OTHER INFORMATION: Coding sequence for humanized light chain CDR
      region of A4 antibody

<400> SEQUENCE: 15

```
gaaattgtgt tgacgcagtc tccaggcacc ctgtctttgt ctccagggga aagagccacc      60
ctctcctgca gggccagtag cagtgttagc agcagctact acactggta ccagcagaaa     120 cctggccagg ctcccaggct cctcatctat agtacgtcca cagggccac tggcatccca     180 gacaggttca gtggcagtgg gtctgggaca gacttcactc tcaccatcag cagactggag     240
cctgaagatt ttgcagtgta ttactgtcag cagtatgaca gctcaccttt cacttttggc     300
caggggacca agctcgagat caaacgt                                          327
```

<210> SEQ ID NO 16
<211> LENGTH: 348
<212> TYPE: DNA
<213> ORGANISM: Artificial Sequence
<220> FEATURE:
<223> OTHER INFORMATION: Coding sequence for humanized heavy chain CDR
      region of A4 antibody

<400> SEQUENCE: 16

```
caggtgcagc tggtgcagtc tggggctgag gtgaagaagc ctggggcctc agtgaaggtc      60
tcctgcaagg cttctggata caccttcacc atcttttgga tgcactgggt gcgacaggcc     120
```

```
cctggacaag ggcttgagtg gatgggaaac atctaccctg gcagtggtgg cacaaactat    180
gcacagaagt tcagggcag ggtcaccatg accagggaca cgtccatcag cacagcctac    240
atggagctga gcaggctgag atctgacgac acggccgtgt attactgtac gagatgggga    300
acgggcaagg actactgggg ccaaggaacc ctggtcaccg tctcctca                348
```

```
<210> SEQ ID NO 17
<211> LENGTH: 16
<212> TYPE: PRT
<213> ORGANISM: Mus musculus
<220> FEATURE:
<221> NAME/KEY: Binding
<222> LOCATION: (1)..(16)
<223> OTHER INFORMATION: amino acid sequence of CDR1 of variable light
      chain region of antibody A3 (mus musculus)

<400> SEQUENCE: 17

Arg Ser Ser Gln Ser Ile Val His Ser Tyr Gly Asn Thr Tyr Leu Glu
1               5                   10                  15

<210> SEQ ID NO 18
<211> LENGTH: 7
<212> TYPE: PRT
<213> ORGANISM: Mus musculus
<220> FEATURE:
<221> NAME/KEY: Binding
<222> LOCATION: (1)..(7)
<223> OTHER INFORMATION: amino acid sequence of CDR2 of variable light
      chain region of antibody A3 (mus musculus)

<400> SEQUENCE: 18

Arg Val Ser Asn Arg Phe Ser
1               5

<210> SEQ ID NO 19
<211> LENGTH: 9
<212> TYPE: PRT
<213> ORGANISM: Mus musculus
<220> FEATURE:
<221> NAME/KEY: Binding
<222> LOCATION: (1)..(9)
<223> OTHER INFORMATION: amino acid sequence of CDR3 of variable light
      chain region of antibody A3 (mus musculus)

<400> SEQUENCE: 19

Phe Gln Gly Ser His Val Pro Phe Thr
1               5

<210> SEQ ID NO 20
<211> LENGTH: 7
<212> TYPE: PRT
<213> ORGANISM: Mus musculus
<220> FEATURE:
<221> NAME/KEY: Binding
<222> LOCATION: (1)..(7)
<223> OTHER INFORMATION: amino acid sequence of CDR1 of variable heavy
      chain region of antibody A3 (mus musculus)

<400> SEQUENCE: 20

Thr Tyr Gly Met Gly Val Gly
1               5

<210> SEQ ID NO 21
<211> LENGTH: 16
<212> TYPE: PRT
<213> ORGANISM: Mus musculus
<220> FEATURE:
<221> NAME/KEY: Binding
```

```
<222> LOCATION: (1)..(16)
<223> OTHER INFORMATION: amino acid sequence of CDR2 of variable heavy
      chain region of antibody A3 (mus musculus)

<400> SEQUENCE: 21

Asn Ile Trp Trp Asn Asp Asp Lys Tyr Tyr Asn Ser Ala Leu Lys Ser
1               5                   10                  15

<210> SEQ ID NO 22
<211> LENGTH: 10
<212> TYPE: PRT
<213> ORGANISM: Mus musculus
<220> FEATURE:
<221> NAME/KEY: Binding
<222> LOCATION: (1)..(10)
<223> OTHER INFORMATION: amino acid sequence of CDR3 of variable heavy
      chain region of antibody A3 (mus musculus)

<400> SEQUENCE: 22

Ile Ala Asn Pro Tyr Trp Tyr Phe Asp Val
1               5                   10

<210> SEQ ID NO 23
<211> LENGTH: 12
<212> TYPE: PRT
<213> ORGANISM: Mus musculus
<220> FEATURE:
<221> NAME/KEY: Binding
<222> LOCATION: (1)..(12)
<223> OTHER INFORMATION: amino acid sequence of CDR1 of variable light
      chain region of antibody A4 (mus musculus)

<400> SEQUENCE: 23

Arg Ala Arg Ser Ser Val Ser Ser Ser Tyr Leu His
1               5                   10

<210> SEQ ID NO 24
<211> LENGTH: 7
<212> TYPE: PRT
<213> ORGANISM: Mus musculus
<220> FEATURE:
<221> NAME/KEY: Binding
<222> LOCATION: (1)..(7)
<223> OTHER INFORMATION: amino acid sequence of CDR2 of variable light
      chain region of antibody A4 (mus musculus)

<400> SEQUENCE: 24

Ser Thr Ser Asn Leu Ala Leu
1               5

<210> SEQ ID NO 25
<211> LENGTH: 9
<212> TYPE: PRT
<213> ORGANISM: Mus musculus
<220> FEATURE:
<221> NAME/KEY: Binding
<222> LOCATION: (1)..(9)
<223> OTHER INFORMATION: amino acid sequence of CDR3 of variable light
      chain region of antibody A4 (mus musculus)

<400> SEQUENCE: 25

Gln Gln Tyr Asp Ser Ser Pro Phe Thr
1               5

<210> SEQ ID NO 26
<211> LENGTH: 5
<212> TYPE: PRT
<213> ORGANISM: Mus musculus
<220> FEATURE:
```

```
<221> NAME/KEY: Binding
<222> LOCATION: (1)..(5)
<223> OTHER INFORMATION: amino acid sequence of CDR1 of variable heavy
      chain region of antibody A4 (mus musculus)

<400> SEQUENCE: 26

Ile Phe Trp Ile His
1               5

<210> SEQ ID NO 27
<211> LENGTH: 17
<212> TYPE: PRT
<213> ORGANISM: Mus musculus
<220> FEATURE:
<221> NAME/KEY: Binding
<222> LOCATION: (1)..(17)
<223> OTHER INFORMATION: amino acid sequence of CDR2 of variable heavy
      chain region of antibody A4 (mus musculus)

<400> SEQUENCE: 27

Asn Ile Tyr Pro Gly Ser Gly Gly Thr Asn Tyr Asp Glu Lys Phe Lys
1               5                   10                  15

Ser

<210> SEQ ID NO 28
<211> LENGTH: 7
<212> TYPE: PRT
<213> ORGANISM: Mus musculus
<220> FEATURE:
<221> NAME/KEY: Binding
<222> LOCATION: (1)..(7)
<223> OTHER INFORMATION: amino acid sequence of CDR3 of variable heavy
      chain region of antibody A4 (mus musculus)

<400> SEQUENCE: 28

Trp Gly Thr Gly Lys Asp Tyr
1               5

<210> SEQ ID NO 29
<211> LENGTH: 12
<212> TYPE: PRT
<213> ORGANISM: Artificial sequence
<220> FEATURE:
<223> OTHER INFORMATION: amino acid sequence of CDR1 of variable light
      chain region of humanized antibody A4

<400> SEQUENCE: 29

Arg Ala Ser Ser Ser Val Ser Ser Ser Tyr Leu His
1               5                   10

<210> SEQ ID NO 30
<211> LENGTH: 7
<212> TYPE: PRT
<213> ORGANISM: Artificial sequence
<220> FEATURE:
<223> OTHER INFORMATION: amino acid sequence of CDR2 of variable light
      chain region of humanized antibody A4

<400> SEQUENCE: 30

Ser Thr Ser Asn Arg Ala Thr
1               5

<210> SEQ ID NO 31
<211> LENGTH: 5
<212> TYPE: PRT
<213> ORGANISM: Artificial Sequence
<220> FEATURE:
<223> OTHER INFORMATION: amino acid sequence of CDR1 of variable heavy
``` chain region of humanized antibody A4

<400> SEQUENCE: 31

Ile Phe Trp Met His
1               5

<210> SEQ ID NO 32
<211> LENGTH: 17
<212> TYPE: PRT
<213> ORGANISM: Artificial Sequence
<220> FEATURE:
<223> OTHER INFORMATION: amino acid sequence of CDR2 of variable heavy
      chain region of humanized antibody A4

<400> SEQUENCE: 32

Asn Ile Tyr Pro Gly Ser Gly Gly Thr Asn Tyr Ala Gln Lys Phe Gln
1               5                   10                  15

Gly

<210> SEQ ID NO 33
<211> LENGTH: 8
<212> TYPE: PRT
<213> ORGANISM: Artificial Sequence
<220> FEATURE:
<223> OTHER INFORMATION: 8 amino acids of the epitope of ErbB3

<400> SEQUENCE: 33

Gln Cys Asn Gly His Cys Phe Gly
1               5

<210> SEQ ID NO 34
<211> LENGTH: 8
<212> TYPE: PRT
<213> ORGANISM: Artificial Sequence
<220> FEATURE:
<223> OTHER INFORMATION: 8 amino acids of the epitope of ErbB3

<400> SEQUENCE: 34

Cys Asn Gly His Cys Phe Gly Pro
1               5

<210> SEQ ID NO 35
<211> LENGTH: 8
<212> TYPE: PRT
<213> ORGANISM: Artificial Sequence
<220> FEATURE:
<223> OTHER INFORMATION: 8 amino acids of the epitope of ErbB3

<400> SEQUENCE: 35

Asn Gly His Cys Phe Gly Pro Asn
1               5

<210> SEQ ID NO 36
<211> LENGTH: 8
<212> TYPE: PRT
<213> ORGANISM: Artificial Sequence
<220> FEATURE:
<223> OTHER INFORMATION: 8 amino acids of the epitope of ErbB3

<400> SEQUENCE: 36

Gly His Cys Phe Gly Pro Asn Pro
1               5

<210> SEQ ID NO 37
<211> LENGTH: 8
<212> TYPE: PRT

```
<213> ORGANISM: Artificial Sequence
<220> FEATURE:
<223> OTHER INFORMATION: 8 amino acids of the epitope of ErbB3

<400> SEQUENCE: 37

His Cys Phe Gly Pro Asn Pro Asn
1               5

<210> SEQ ID NO 38
<211> LENGTH: 8
<212> TYPE: PRT
<213> ORGANISM: Artificial Sequence
<220> FEATURE:
<223> OTHER INFORMATION: 8 amino acids of the epitope of ErbB3

<400> SEQUENCE: 38

Cys Phe Gly Pro Asn Pro Asn Gln
1               5

<210> SEQ ID NO 39
<211> LENGTH: 8
<212> TYPE: PRT
<213> ORGANISM: Artificial Sequence
<220> FEATURE:
<223> OTHER INFORMATION: 8 amino acids of the epitope of ErbB3

<400> SEQUENCE: 39

Phe Gly Pro Asn Pro Asn Gln Cys
1               5

<210> SEQ ID NO 40
<211> LENGTH: 8
<212> TYPE: PRT
<213> ORGANISM: Artificial Sequence
<220> FEATURE:
<223> OTHER INFORMATION: 8 amino acids of the epitope of ErbB3

<400> SEQUENCE: 40

Gly Pro Asn Pro Asn Gln Cys Cys
1               5

<210> SEQ ID NO 41
<211> LENGTH: 9
<212> TYPE: PRT
<213> ORGANISM: Artificial Sequence
<220> FEATURE:
<223> OTHER INFORMATION: 9 amino acids of the epitope of ErbB3

<400> SEQUENCE: 41

Gln Cys Asn Gly His Cys Phe Gly Pro
1               5

<210> SEQ ID NO 42
<211> LENGTH: 9
<212> TYPE: PRT
<213> ORGANISM: Artificial Sequence
<220> FEATURE:
<223> OTHER INFORMATION: 9 amino acids of the epitope of ErbB3

<400> SEQUENCE: 42

Cys Asn Gly His Cys Phe Gly Pro Asn
1               5

<210> SEQ ID NO 43
<211> LENGTH: 9
<212> TYPE: PRT
<213> ORGANISM: Artificial Sequence
```

```
<220> FEATURE:
<223> OTHER INFORMATION: 9 amino acids of the epitope of ErbB3

<400> SEQUENCE: 43

Asn Gly His Cys Phe Gly Pro Asn Pro
1               5

<210> SEQ ID NO 44
<211> LENGTH: 9
<212> TYPE: PRT
<213> ORGANISM: Artificial Sequence
<220> FEATURE:
<223> OTHER INFORMATION: 9 amino acids of the epitope of ErbB3

<400> SEQUENCE: 44

Gly His Cys Phe Gly Pro Asn Pro Asn
1               5

<210> SEQ ID NO 45
<211> LENGTH: 9
<212> TYPE: PRT
<213> ORGANISM: Artificial Sequence
<220> FEATURE:
<223> OTHER INFORMATION: 9 amino acids of the epitope of ErbB3

<400> SEQUENCE: 45

His Cys Phe Gly Pro Asn Pro Asn Gln
1               5

<210> SEQ ID NO 46
<211> LENGTH: 9
<212> TYPE: PRT
<213> ORGANISM: Artificial Sequence
<220> FEATURE:
<223> OTHER INFORMATION: 9 amino acids of the epitope of ErbB3

<400> SEQUENCE: 46

Cys Phe Gly Pro Asn Pro Asn Gln Cys
1               5

<210> SEQ ID NO 47
<211> LENGTH: 9
<212> TYPE: PRT
<213> ORGANISM: Artificial Sequence
<220> FEATURE:
<223> OTHER INFORMATION: 9 amino acids of the epitope of ErbB3

<400> SEQUENCE: 47

Phe Gly Pro Asn Pro Asn Gln Cys Cys
1               5

<210> SEQ ID NO 48
<211> LENGTH: 10
<212> TYPE: PRT
<213> ORGANISM: Artificial Sequence
<220> FEATURE:
<223> OTHER INFORMATION: 10 amino acids of the epitope of ErbB3

<400> SEQUENCE: 48

Gln Cys Asn Gly His Cys Phe Gly Pro Asn
1               5                   10

<210> SEQ ID NO 49
<211> LENGTH: 10
<212> TYPE: PRT
<213> ORGANISM: Artificial Sequence
<220> FEATURE:
```

<223> OTHER INFORMATION: 10 amino acids of the epitope of ErbB3

<400> SEQUENCE: 49

Cys Asn Gly His Cys Phe Gly Pro Asn Pro
1               5                   10

<210> SEQ ID NO 50
<211> LENGTH: 10
<212> TYPE: PRT
<213> ORGANISM: Artificial Sequence
<220> FEATURE:
<223> OTHER INFORMATION: 10 amino acids of the epitope of ErbB3

<400> SEQUENCE: 50

Asn Gly His Cys Phe Gly Pro Asn Pro Asn
1               5                   10

<210> SEQ ID NO 51
<211> LENGTH: 10
<212> TYPE: PRT
<213> ORGANISM: Artificial Sequence
<220> FEATURE:
<223> OTHER INFORMATION: 10 amino acids of the epitope of ErbB3

<400> SEQUENCE: 51

Gly His Cys Phe Gly Pro Asn Pro Asn Gln
1               5                   10

<210> SEQ ID NO 52
<211> LENGTH: 10
<212> TYPE: PRT
<213> ORGANISM: Artificial Sequence
<220> FEATURE:
<223> OTHER INFORMATION: 10 amino acids of epitope of ErbB3

<400> SEQUENCE: 52

His Cys Phe Gly Pro Asn Pro Asn Gln Cys
1               5                   10

<210> SEQ ID NO 53
<211> LENGTH: 10
<212> TYPE: PRT
<213> ORGANISM: Artificial Sequence
<220> FEATURE:
<223> OTHER INFORMATION: 10 amino acids of the epitope of ErbB3

<400> SEQUENCE: 53

Cys Phe Gly Pro Asn Pro Asn Gln Cys Cys
1               5                   10

<210> SEQ ID NO 54
<211> LENGTH: 11
<212> TYPE: PRT
<213> ORGANISM: Artificial Sequence
<220> FEATURE:
<223> OTHER INFORMATION: 11 amino acids of epitope of ErbB3

<400> SEQUENCE: 54

Gln Cys Asn Gly His Cys Phe Gly Pro Asn Pro
1               5                   10

<210> SEQ ID NO 55
<211> LENGTH: 11
<212> TYPE: PRT
<213> ORGANISM: Artificial sequence
<220> FEATURE:
<223> OTHER INFORMATION: 11 amino acids of the epitope of ErbB3

```
<400> SEQUENCE: 55

Cys Asn Gly His Cys Phe Gly Pro Asn Pro Asn
1               5                   10

<210> SEQ ID NO 56
<211> LENGTH: 11
<212> TYPE: PRT
<213> ORGANISM: Artificial Sequence
<220> FEATURE:
<223> OTHER INFORMATION: 11 amino acids of the epitope of ErbB3

<400> SEQUENCE: 56

Asn Gly His Cys Phe Gly Pro Asn Pro Asn Gln
1               5                   10

<210> SEQ ID NO 57
<211> LENGTH: 11
<212> TYPE: PRT
<213> ORGANISM: Artificial Sequence
<220> FEATURE:
<223> OTHER INFORMATION: 11 amino acids of the epitope ErbB3

<400> SEQUENCE: 57

Gly His Cys Phe Gly Pro Asn Pro Asn Gln Cys
1               5                   10

<210> SEQ ID NO 58
<211> LENGTH: 11
<212> TYPE: PRT
<213> ORGANISM: Artificial Sequence
<220> FEATURE:
<223> OTHER INFORMATION: 11 amino acids of the epitope of ErbB3

<400> SEQUENCE: 58

His Cys Phe Gly Pro Asn Pro Asn Gln Cys Cys
1               5                   10

<210> SEQ ID NO 59
<211> LENGTH: 12
<212> TYPE: PRT
<213> ORGANISM: Artificial Sequence
<220> FEATURE:
<223> OTHER INFORMATION: 12 amino acids of the epitope of ErbB3

<400> SEQUENCE: 59

Gln Cys Asn Gly His Cys Phe Gly Pro Asn Pro Asn
1               5                   10

<210> SEQ ID NO 60
<211> LENGTH: 12
<212> TYPE: PRT
<213> ORGANISM: Artificial sequence
<220> FEATURE:
<223> OTHER INFORMATION: 12 amino acids of the epitope of ErbB3

<400> SEQUENCE: 60

Cys Asn Gly His Cys Phe Gly Pro Asn Pro Asn Gln
1               5                   10

<210> SEQ ID NO 61
<211> LENGTH: 12
<212> TYPE: PRT
<213> ORGANISM: Artificial Sequence
<220> FEATURE:
<223> OTHER INFORMATION: 12 amino acids of the epitope of ErbB3
```

```
<400> SEQUENCE: 61

Asn Gly His Cys Phe Gly Pro Asn Pro Asn Gln Cys
1               5                   10

<210> SEQ ID NO 62
<211> LENGTH: 12
<212> TYPE: PRT
<213> ORGANISM: Artificial Sequence
<220> FEATURE:
<223> OTHER INFORMATION: 12 amino acids of the epitope of ErbB3

<400> SEQUENCE: 62

Gly His Cys Phe Gly Pro Asn Pro Asn Gln Cys Cys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: 13 amino acids of the epitope of ErbB3

<400> SEQUENCE: 63

Gln Cys Asn Gly His Cys Phe Gly Pro Asn Pro Asn Gln
1               5                   10

<210> SEQ ID NO 64
<211> LENGTH: 13
<212> TYPE: PRT
<213> ORGANISM: Artificial Sequence
<220> FEATURE:
<223> OTHER INFORMATION: 13 amino acids of the epitope of ErbB3

<400> SEQUENCE: 64

Cys Asn Gly His Cys Phe Gly Pro Asn Pro Asn Gln Cys
1               5                   10

<210> SEQ ID NO 65
<211> LENGTH: 13
<212> TYPE: PRT
<213> ORGANISM: Artificial Sequence
<220> FEATURE:
<223> OTHER INFORMATION: 13 amino acids of the epitope of ErbB3

<400> SEQUENCE: 65

Asn Gly His Cys Phe Gly Pro Asn Pro Asn Gln Cys Cys
1               5                   10

<210> SEQ ID NO 66
<211> LENGTH: 14
<212> TYPE: PRT
<213> ORGANISM: Artificial Sequence
<220> FEATURE:
<223> OTHER INFORMATION: 14 amino acids of the epitope of ErbB3

<400> SEQUENCE: 66

Cys Asn Gly His Cys Phe Gly Pro Asn Pro Asn Gln Cys Cys
1               5                   10

<210> SEQ ID NO 67
<211> LENGTH: 14
<212> TYPE: PRT
<213> ORGANISM: Artificial Sequence
<220> FEATURE:
<223> OTHER INFORMATION: 14 amino acids of the epitope of ErbB3

<400> SEQUENCE: 67
```

```
Gln Cys Asn Gly His Cys Phe Gly Pro Asn Pro Asn Gln Cys
1               5                   10

<210> SEQ ID NO 68
<211> LENGTH: 15
<212> TYPE: PRT
<213> ORGANISM: Artificial Sequence
<220> FEATURE:
<223> OTHER INFORMATION: 15 amino acids of the epitope of ErbB3

<400> SEQUENCE: 68

Gln Cys Asn Gly His Cys Phe Gly Pro Asn Pro Asn Gln Cys Cys
1               5                   10                  15
```